US011136345B2

(12) United States Patent
Mizhiritskii et al.

(10) Patent No.: US 11,136,345 B2
(45) Date of Patent: Oct. 5, 2021

(54) LARGE SCALE PREPARATION OF PSEUDO-TRISACCHARIDE AMINOGLYCOSIDES AND OF INTERMEDIATES THEREOF

(71) Applicant: Eloxx Pharmaceuticals Ltd., Rehovot (IL)

(72) Inventors: Michael Mizhiritskii, Rehovot (IL); Mani Bushan Kotala, Kompally (IN); Ravinder Palidi, Nagarkurnool (IN)

(73) Assignee: ELOXX PHARMACEUTICALS LTD., Rehovot (IL)

( * ) Notice: Subject to any disclaimer, the term of this patent is extended or adjusted under 35 U.S.C. 154(b) by 0 days.

(21) Appl. No.: 16/493,732

(22) PCT Filed: Mar. 15, 2018

(86) PCT No.: PCT/IL2018/050306
§ 371 (c)(1),
(2) Date: Sep. 12, 2019

(87) PCT Pub. No.: WO2018/167794
PCT Pub. Date: Sep. 20, 2018

(65) Prior Publication Data
US 2020/0079809 A1 Mar. 12, 2020

(30) Foreign Application Priority Data
Mar. 15, 2017 (IN) .............................. 201721008996

(51) Int. Cl.
*C07H 15/224* (2006.01)
*C07H 1/00* (2006.01)
*C07H 15/23* (2006.01)

(52) U.S. Cl.
CPC ............. *C07H 15/224* (2013.01); *C07H 1/00* (2013.01); *C07H 15/23* (2013.01)

(58) Field of Classification Search
None
See application file for complete search history.

(56) References Cited

U.S. PATENT DOCUMENTS

| | | |
|---|---|---|
| 3,897,412 A | 7/1975 | Naito et al. |
| 3,996,205 A | 12/1976 | Magerlein |
| 4,024,332 A | 5/1977 | Fenner et al. |
| 4,029,882 A | 6/1977 | Wright |
| 4,170,641 A | 10/1979 | Akita et al. |

FOREIGN PATENT DOCUMENTS

| | | |
|---|---|---|
| FR | 2427341 A1 | 12/1979 |
| JP | 0446189 A | 2/1992 |
| WO | 2007113841 A2 | 10/2007 |
| WO | 2011044538 A1 | 4/2011 |
| WO | 2012066546 A1 | 5/2012 |
| WO | 2015186134 A1 | 12/2015 |
| WO | 2017037717 A1 | 3/2017 |
| WO | 2017037718 A1 | 3/2017 |
| WO | 2017037719 A1 | 3/2017 |

OTHER PUBLICATIONS

WIPO, International Search Report and Written Opinion for International Application No. PCT/IL2018/050306. dated Jun. 17, 2018. 17 pages.
WIPO, International Search Report and Written Opinion for International Application No. PCT/IL2018/050612. dated Aug. 22, 2018. 13 pages.
Akita, E. et al. "Synthesis of 1-N-(2-Aminoethanesulfonyl)-Kanamycins and Related Aminoglycoside Antibiotics" The Journal of Antibiotics, 1983, vol. 36, No. 6, pp. 745-748.
Azimov, R. et al. "G418-mediated ribosomal read-through of a nonsense mutation causing autosomal recessive proximal renal tubular acidosis" Am. J. Physiol. Renal Physiol., 2008, vol. 295, F633-F641.
Bidou, L. et al. "Characterization of new-generation aminoglycoside promoting premature termination codon readthrough in cancer cells" RNA Biology, 2017, vol. 14, No. 3, pp. 378-388.
Brendel, C. et al. "Readthrough of nonsense mutations in Rett syndrome: Evaluation of novel aminoglycosides and generation of a new mouse model" Journal of Molecular Medicine, 2011, vol. 89, No. 3, pp. 389-398.
Dondoni, A. et al. "Stereoselective Homologation—Amination of Aldehydes by Addition of Their Nitrones to C-2 Metalated Thiazoles—A General Entry to α-Amino Aldehydes and Amino Sugars" Chem. Eur. J., 1995, vol. 1, No. 8, pp. 505-520.
Dondoni, A. et al. "Stereoselective Addition of 2-Furyllithium and 2-Thiazolyllithium to Sugar Nitrones. Synthesis of Carbon-Linked Glycoglycines" J. Org. Chem., 1997, vol. 62, pp. 5484-5496.
Dondoni, A. et al. "Applications of Sugar Nitrones in Synthesis: The Total Synthesis of (+)- Polyoxin J¹" J. Org. Chem., 1997, vol. 62, pp. 5497-5507.
Duscha, S. et al. "Identification and Evaluation of Improved 4"-O-(Alkyl) 4,5-Disubstituted 2-Deoxystreptamines as Next-Generation Aminoglycoside Antibiotics" mBio, 2014, vol. 5, No. 5, 10 pages.
Garreau de Loubresse, N. et al. "Structural basis for the inhibition of the eukaryotic ribosome" Nature, 2014, vol. 513, 18 pages.
Goldmann, T. et al. "Beneficial Read-Through of a USH1C Nonsense Mutation by Designed Aminoglycoside NB30 in the Retina" Physiology and Pharmacology, 2010, vol. 51, No. 12, pp. 6671-6680.
Greenberg, W. et al. "Design and Synthesis of New Aminoglycoside Antibiotics Containing Neamine as an Optimal Core Structure: Correlation of Antibiotic Activity with in Vitro Inhibition of Translation" J. Am. Chem. Soc., 1999, vol. 121, pp. 6527-6541.

(Continued)

*Primary Examiner* — Layla D Berry
(74) *Attorney, Agent, or Firm* — Perkins Coie LLP

(57) ABSTRACT

Synthetic pathways for preparing pseudo-trisaccharide aminoglycoside compounds represented by Formula I or Ia as defined in the specification and donor and acceptor compounds useful for preparing such compounds are provided. A process of stereoselectively preparing compounds represented by Formula III as defined in the specification, while avoiding chromatographic separation of stereoisomers are also provided. Compounds prepared by the described processes and uses thereof are also provided.

14 Claims, 6 Drawing Sheets

(56) References Cited

OTHER PUBLICATIONS

Figure 1:
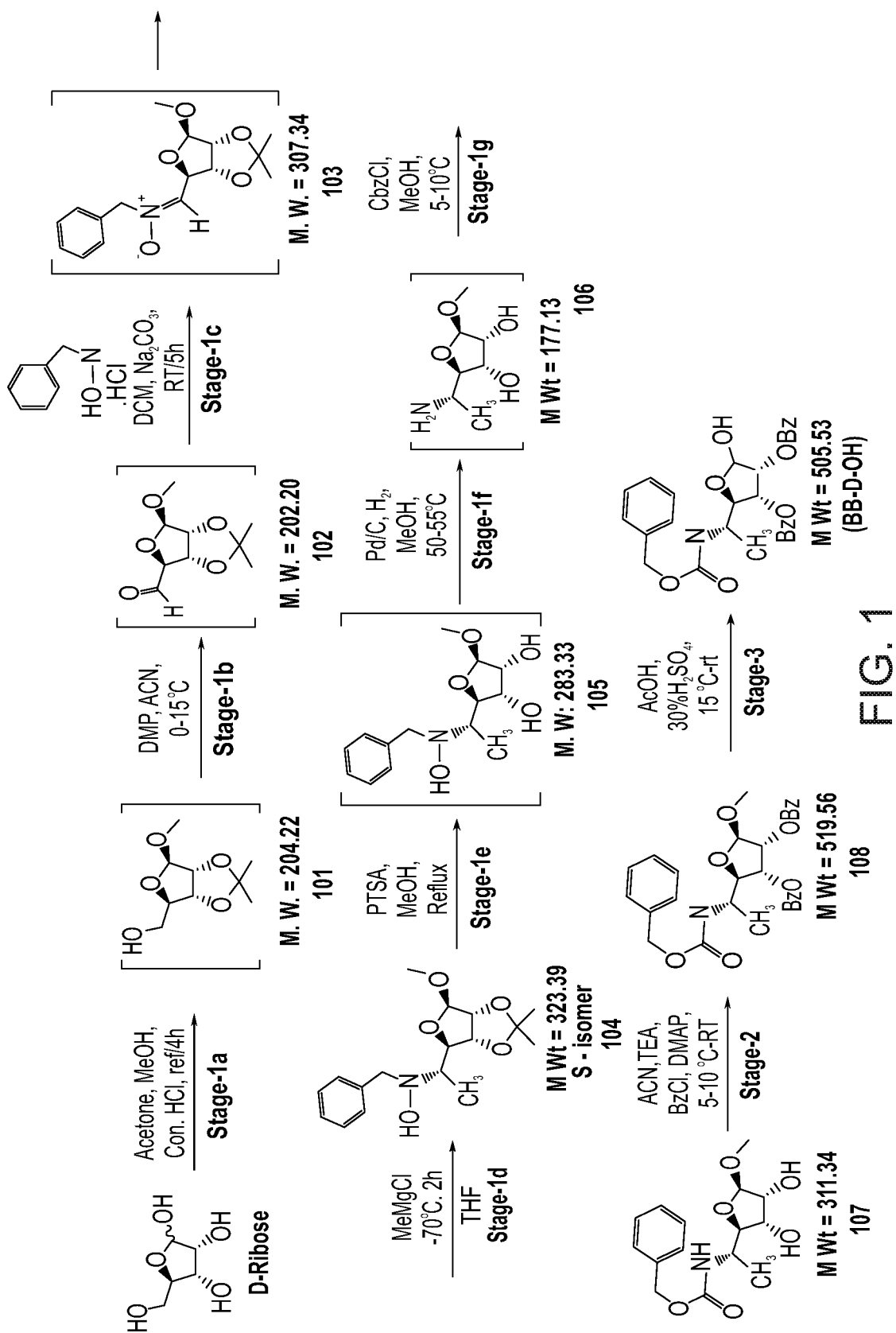

Gunn, G. et al. "Long-Term Nonsense Suppression Therapy Moderates MPS I-H Disease Progression" Mol Genet Metab., 2014, vol. 111, No. 3, pp. 374-381.
Haddad, J. et al. "Design of Novel Antibiotics that Bind to the Ribosomal Acyltransfer Site" J. Am. Chem. Soc., 2002, vol. 124, No. 13, pp. 3229-3237.
Hainrichson, M. et al. "Designer aminoglycosides: the race to develop improved antibiotics and compounds for the treatment of human genetic diseases" Organic and Biomolecular Chemistry, 2008, vol. 6, pp. 227-239.
Hobbie, S. et al. "Engineering the rRNA decoding site of eukaryotic cytosolic ribosomes in bacteria" Nucleic Acids Research, 2007, vol. 35, No. 18, pp. 6068-6093.
Hobbie, S. et al. "Genetic analysis of interactions with eukaryotic rRNA identify the mitoribosome as target in aminoglycoside ototoxicity" PNAS, 2008, vol. 105, No. 52, pp. 20888-20893.
Hobbie, S. et al. "Mitochondrial deafness alleles confer misreading of the genetic code" PNAS, 2008, vol. 105, No. 9, pp. 3244-3249.
Huth, M. et al. "Designer aminoglycosides prevent cochlear hair cell loss and hearing loss" Journal of Clinical Investigation, 2015, vol. 125, No. 2, pp. 583-592.
Kandasamy, J. et al. "Increased Selectivity toward Cytoplasmic versus Mitochondrial Ribosome Confers Improved Efficiency of Synthetic Aminoglycosides in Fixing Damaged Genes: A Strategy for Treatment of Genetic Diseases Caused by Nonsense Mutations" Journal of Medicinal Chemistry, 2012, vol. 55, pp. 10630-10643.
Kato, T. et al. "Synthesis and Antiribosomal Activities of 4'-O-, 6'-O-, 4''-O-, 4',6'-O- and 4'',6''-O-Derivatives in the Kanamycin Series Indicate Differing Target Selectivity Patterns between the 4,5- and 4,6-Series of Disubstituted 2-Deoxystreptamine Aminoglycoside Antibiotics" ICS Infectious Diseases, 2015, vol. 1, pp. 479-486.
Keeling, K. et al. "Attenuation of Nonsense-Mediated mRNA Decay Enhances In Vivo Nonsense Suppression" PLOS ONE, 2013, vol. 8, No. 4, 11 pages.
Kondo, J. et al. "Differential Selectivity of Natural and Synthetic Aminoglycosides towards the Eukaryotic and Prokaryotic Decoding A Sites" ChemBioChem, 2007, vol. 8, pp. 1700-1709.
Kotra, L. et al. "Aminoglycosides: Perspectives on Mechanisms of Action and Resistance and Strategies to Counter Resistance" Antimicrobial Agents and Chemotherapy, 2000, pp. 3249-3256.
Lopez-Novoa, J. et al. "New insights into the mechanism of aminoglycoside nephrotoxicity: an integrative point of view" Kidney International, 2010, 13 pages.
Malik, V. et al. "Aminoglycoside-induced mutation suppression (stop codon readthrough) as a therapeutic strategy for Duchenne muscular dystrophy" Therapeutic Advances in Neurological Disorders, 2010, vol. 3, pp. 379-389.
Martin, O. et al. "Synthetic Routes from Paromamine to the Octodiose-Containing Pseudodisaccharide present in (Oxy)Apramycin" Carbohydrate Research, 1984, vol. 130, pp. 195-219.
Nudelman, I. et al. "Combined Chemical-Enzymatic Assembly of Aminoglycoside Derivatives with N-1-AHB Side Chain" Advanced Synthesis & Catalysis, 2008, vol. 350, pp. 1682-1688.
Nudelman, I. et al. "Development of Novel Aminoglycoside (NB54) with Reduced Toxicity and Enhanced Suppression of Disease-Causing Premature Stop Mutations" Journal of Medicinal Chemistry, 2009, vol. 52, No. 9, pp. 2836-2845.
Nudelman, I. et al. "Redesign of aminoglycosides for treatment of human genetic diseases caused by premature stop mutations" Bioorganic & Medicinal Chemistry Letters, 2006, vol. 16, pp. 6310-6315.
Nudelman, I. et al. "Repairing faulty genes by aminoglycosides: Development of new derivatives of geneticin (G418) with enhanced suppression of diseases-causing nonsense mutations" Bioorganic & Medicinal Chemistry, 2010, vol. 18, pp. 3735-3746.
Perez-Fernandez, D. et al. "4'-O-substitutions determine selectivity of aminoglycoside antibiotics" Nature Communications, 2014, 12 pages.
Rebibo-Sabbah, A. et al. "In vitro and ex vivo suppression by aminoglycosides of PCDH15 nonsense mutations underlying type 1 Usher syndrome" Human Genetics, 2007, vol. 122, pp. 373-381.
Rowe, S. et al. "Suppression of CFTR premature termination codons and rescue of CFTR protein and function by the synthetic aminoglycoside NB54" Journal of Molecular Medicine, 2011, 13 pages.
Sabbavarapu, N. et al. "Design of Novel Aminoglycoside Derivatives with Enhanced Suppression of Diseases-Causing Nonsense Mutations" Medicinal Chemistry Letters, 2016, vol. 7, No. 4, pp. 418-423.
Shalev, M. et al. "Identification of the molecular attributes required for aminoglycoside activity against Leishmania" PNAS, 2013, vol. 110, No. 33, pp. 13333-13338.
Shalev, M. et al. "Structural basis for selective targeting of leishmanial ribosomes: aminoglycoside derivatives as promising therapeutics" Nucleic Acids Research, 2015, vol. 43, No. 17, pp. 8601-8613.
Shulman, E. et al. "Designer Aminoglycosides That Selectively Inhibit Cytoplasmic Rather than Mitochondrial Ribosomes Show Decreased Ototoxicity" Journal of Biological Chemistry, vol. 289, No. 4, pp. 2318-2330.
Simonsen, K. et al. "Novel Paromamine Derivatives Exploring Shallow-Groove Recognition of Ribosomal-Decoding-Site RNA" ChemBioChem, 2002, vol. 3, pp. 1223-1228.
Thiverny, M. et al. "Totally diastereoselective addition of aryl Grignard reagents to the nitrone-based chiral glycine equivalent MiPNO" Tetrahedron: Asymmetry, 2011, vol. 22, pp. 1274-1281.
Vecsler, M. et al. "Ex Vivo Treatment with a Novel Synthetic Aminoglycoside NB54 in Primary Fibroblasts from Rett Syndrome Patients Suppresses MECP2 Nonsense Mutations" PLOS ONE, 2011, vol. 6, No. 6, 8 pages.
Venkataraman, N. et al. "Reawakening Retrocyclins: Ancestral Human Defensins Active Against HIV-1" PLOS Biology, 2009, vol. 7, No. 4, pp. 720-729.
Wang, D. et al. "The Designer Aminoglycoside NB84 Significantly Reduces Glycosaminoglycan Accumulation Associated with MPS I-H in the Idua-W392X Mouse" Molecular Genetics and Metabolism, 2012, vol. 105, No. 1, pp. 116-125.
Warchol, M. "Cellular mechanisms of aminoglycoside ototoxicity" Current Opinion in Otolaryngology & Head and Neck Surgery, 2010, vol. 18, No. 5, pp. 454-458.
Eurasian Patent Office, Official Action for Eurasian Patent Application No. 201992804. dated Oct. 27, 2020. 11 pages with English translation.
EPO, Extended European Search Report for European Patent Application No. 18767330.6. dated Dec. 8, 2020. 10 pages.
EPO, Extended European Search Report for European Patent Application No. 18814198.0. dated Feb. 22, 2021. 9 pages.
Gao, F. et al. "Synthesis and use of sulfonamide-, sulfoxide-, or sulfone-containing aminoglycoside-CoA bisubstrates as mechanistic probes for aminoglycoside N-6-acetyltransferase" Bioorganic & Medicinal Chemistry Letters, 2008, vol. 18. pp. 5518-5522.
IPCM, Preliminary Examination Report for Malaysian Patent Application No. PI2019007150. dated May 30, 2020. 3 pages.
IPI, Examination Report for Indian Patent Application No. 201947041644. dated Mar. 31, 2021. 6 pages.
IPS, Written Opinion for Singaporean Patent Application No. 11201911480T. dated Oct. 5, 2020. 6 pages.
Merino, P. et al. "A General Method for the Vinylation of Nitrones. Synthesis of Allyl Hydroxylamines and Allyl Amines" Synthetic Communications, 2000, vol. 30, No. 16, pp. 2989-3021.
Rehak, J. et al. "Samarium diiodide-induced reductive coupling of chiral nitrones with methyl acrylate" ARKIVOC, 2008, vol. 7, pp. 18-27.

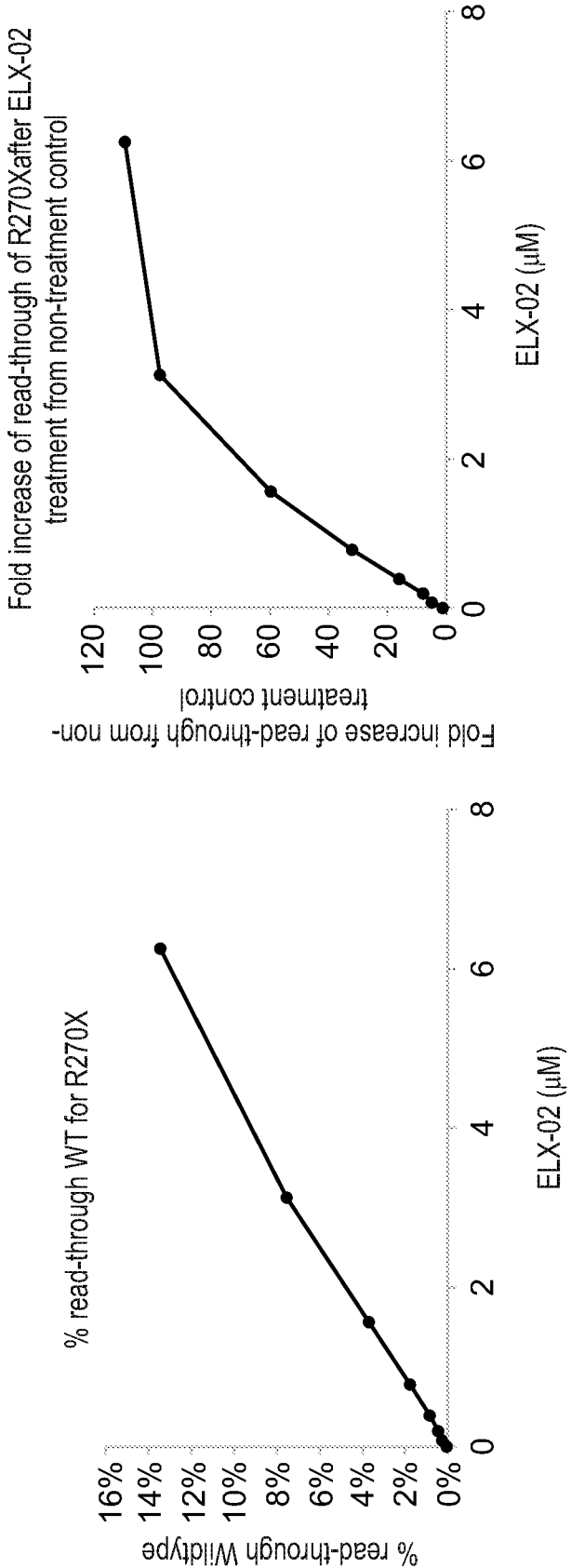

LARGE SCALE PREPARATION OF PSEUDO-TRISACCHARIDE AMINOGLYCOSIDES AND OF INTERMEDIATES THEREOF

CROSS-REFERENCE TO RELATED APPLICATIONS

This patent document is a 371 National Phase Application of PCT Application No. PCT/USIL2018/050306 entitled "LARGE SCALE PREPARATION OF PSEUDO-TRISACCHARIDE AMINOGLYCOSIDES AND OF INTERMEDIATES THEREOF" filed on Mar. 15, 2018, which claims the benefit of priority of Indian Patent Application No. 201721008996 filed on Mar. 15, 2017. The entire contents of the aforementioned patent applications are incorporated by reference as part of the disclosure of this patent application.

FIELD AND BACKGROUND OF THE INVENTION

The present invention, in some embodiments thereof, relates to synthesis of aminoglycosides and, more particularly, but not exclusively, to novel processes of preparing pseudo-trisaccharide aminoglycosides which exhibit read-through activity and reduced toxicity, useful for large scale production of such aminoglycosides and of acceptor and donor intermediate compounds useful for preparing such aminoglycosides.

Many human genetic disorders result from nonsense mutations, where one of the three stop codons (UAA, UAG or UGA) replaces an amino acid-coding codon, leading to premature termination of the translation and eventually to truncated inactive proteins. Currently, hundreds of such nonsense mutations are known, and several were shown to account for certain cases of fatal diseases, including, for example, cystic fibrosis (CF), Duchenne muscular dystrophy (DMD), ataxia-telangiectasia, Hurler syndrome, hemophilia A, hemophilia B, Tay-Sachs, and more. For many of those diseases there is presently no effective treatment.

Aminoglycosides are highly potent, broad-spectrum antibiotics commonly used for the treatment of life-threatening infections. Some aminoglycoside compounds have been shown to have therapeutic value in the treatment of several genetic diseases because of their ability to induce ribosomes to read-through stop codon mutations, generating full-length proteins from part of the mRNA molecules.

However, most of the aminoglycoside compounds which exhibit significant effect on cytoplasmic ribosomes of human cells, exhibit also an antimicrobial activity and/or otherwise toxicity to mammalian cells. Antimicrobial activity of a read-through drug is undesirable as any unnecessary use of antibiotics, particularly with respect to the gastrointestinal (GI) biota, due to the adverse effects caused by upsetting the GI biota equilibrium and the emergence of resistance.

Extensive studies have been made to uncover aminoglycoside compounds, which can be beneficially used in the treatment of genetic diseases, by exhibiting high premature stop codon mutations read-through activity, low toxicity in mammalian cells and low antimicrobial activity, as well as improved bioavailability and/or cell permeability.

WO 2007/113841, which is incorporated by reference as if fully set forth herein, teaches a class of paromomycin-derived aminoglycosides, which were designed specifically to exhibit high premature stop codon mutations readthrough activity while exerting low cytotoxicity in mammalian cells and low antimicrobial activity, and can thus be used in the treatment of genetic diseases. This class of paromomycin-derived aminoglycosides was designed by introducing certain manipulations of a paromamine core, which lead to enhanced readthrough activity and reduced toxicity and antimicrobial activity. The manipulations were made on several positions of the paromamine core.

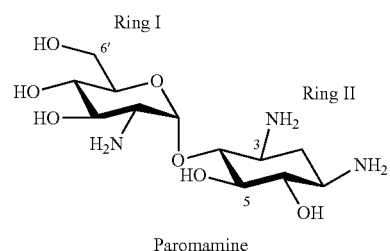

Paromamine

One such manipulation of the paromamine core which has been described in WO 2007/113841 is the determination of the beneficial role of a hydroxyl group at position 6' of the aminoglycoside core.

Another manipulation of the paromamine core which has been defined and demonstrated in WO 2007/113841 is the introduction of one or more monosaccharide moieties or an oligosaccharide moiety at position 3', 5 and/or 6 of the aminoglycoside core.

An additional manipulation of the paromamine core which has been defined and demonstrated in WO 2007/113841 is the introduction of an (S)-4-amino-2-hydroxybutyryl (AHB) moiety at position 1 of the paromamine core.

An additional manipulation of the paromamine core which has been described in WO 2007/113841 is the substitution of hydrogen at position 6' by an alkyl such as a methyl substituent.

WO 2012/066546, which is also incorporated by reference as if fully set forth herein, discloses another class of pseudo-trisaccharide aminoglycosides, which exhibit efficient stop codon mutation read-through activity, low cytotoxicity and high selectivity towards eukaryotic translation systems. These pseudo-trisaccharide aminoglycosides feature an alkyl group at the 5" position, as exemplified for compound NB124.

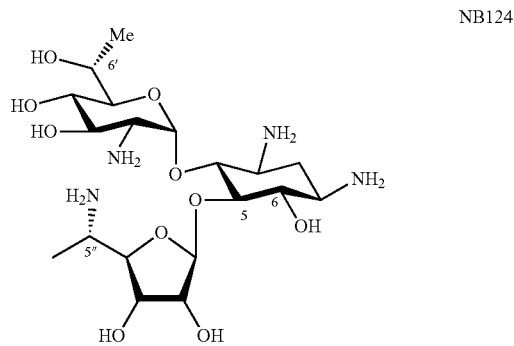

WO 2012/066546 further discloses improved performance of the stereoisomers that feature an S-configuration at the 5" position.

The syntheses of the pseudo-trisaccharide aminoglycoside compounds disclosed in WO 2007/113841 and WO 2012/066546 are based on coupling a donor mono-saccharide moiety (which forms Ring III of the aminoglycoside compound) to a pseudo disaccharide acceptor. The pseudo-disaccharide acceptor, according to the teachings of WO 2007/113841 and WO 2012/066546, can be obtained by cleavage of paromomycin, so as to obtain a paromamine disaccharide core, which is further manipulated as desired. The synthetic pathways involve a use of amino-protecting groups, typically azides, a use of hydroxy-protecting groups, and chromatographic separations of stereoisomers at various stages of the syntheses.

Additional background art includes Nudelman, I., et al., Bioorg Med Chem Lett, 2006. 16(24): p. 6310-5; Nudelman, I., et al., Bioorg Med Chem, 2010. 18(11): p. 3735-46; WO 2017/037717 and WO 2017/037718.

SUMMARY OF THE INVENTION

The present inventors have now designed and successfully practiced a novel synthetic pathway for producing pseudo-trisaccharide aminoglycosides, such as described in WO 2012/066546 and in WO 2017/037718, which is suitable for large-scale production of such aminoglycoside compounds. The newly designed process, while being based on coupling a monosaccharide donor with a pseudo-disaccharide acceptor, as previously described, beneficially uses G-418 as a starting material for preparing the acceptor, and, importantly, uses a stereoselective synthesis of a desired stereoisomer of the donor, thereby circumventing the need to use chromatographic separation of stereoisomers. The newly designed process is further advantageously characterized by a reduced number of steps, substantially reduced number of chromatographic separations, by reduced or eliminated use of hazardous reagents, by higher yields and improved cost effectiveness.

Some embodiments of the present invention therefore relate to a novel process of preparing a desired stereoisomer of a donor glycosyl compound, to a novel process of coupling such a donor to a suitable acceptor to thereby obtain a pseudo-trisaccharide aminoglycoside compound such as described in WO 2012/066546 and WO 2017/037718, to a novel process of preparing a pseudo-disaccharide acceptor as described herein, and to a novel process of coupling the donor and acceptor as described herein and generating the final pseudo-trisaccharide aminoglycoside thereupon. Some embodiments of the present invention relate to a large scale production of a stereoisomer of a donor glycosyl compound as described herein (e.g., a compound represented by Formula III). Some embodiments of the present invention relate to a large scale production of pseudo-trisaccharide aminoglycoside compounds such as described in WO 2012/066546 and WO 2017/037718 (e.g., compounds represented by Formula I or Ia).

Some embodiments of the present invention relate to donor compounds, acceptor compounds, pseudo-trisaccharide aminoglycosides and other intermediate compounds, prepared by the processes as described herein.

According to an aspect of some embodiments of the present invention there is provided a process of preparing a compound represented by Formula III:

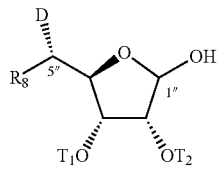

Formula III wherein:

$OT_1$ and $OT_2$ are each independently a donor protected hydroxyl group;

$R_8$ is alkyl, preferably methyl; and

D is a protected amino group, the process being for large scale preparation (large scale production or manufacturing, as defined herein) of the compound of Formula III, or of a compound represented by Formula I or Ia as described herein.

According to an aspect of some embodiments of the present invention there is provided a process of preparing a compound represented by Formula III:

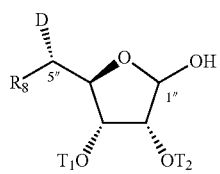

Formula III wherein:

$OT_1$ and $OT_2$ are each independently a donor protected hydroxyl group;

$R_8$ is alkyl, preferably methyl; and

D is a protected amino group, the process comprising:

reacting a compound represented by Formula IIIa:

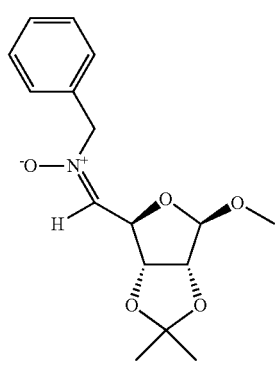

Formula IIIa with a Grignard reagent represented by the Formula $R_8MgX$, wherein X is halide, to thereby obtain stereoselectively a compound represented by Formula IIIb, featuring an S-configuration as indicated below:

Formula IIIb

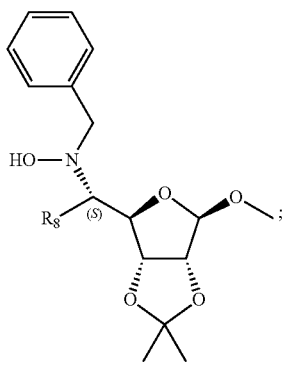

converting the compound represented by Formula IIIb to a compound represented by Formula IIIc:

Formula IIIc

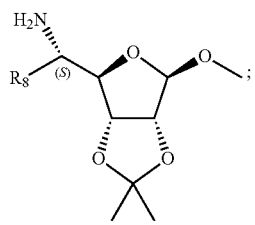

reacting the compound represented by Formula IIIc with an amino-protecting group to thereby form the D; and reacting the compound represented by Formula IIIc with hydroxy protecting groups to thereby form the $OT_1$ and $OT_2$, thereby preparing the compound represented by Formula III.

According to some of any of the embodiments described herein, the amino-protecting group is N-benzyloxycarbonyl.

According to some of any of the embodiments described herein, each of the hydroxy-protecting groups is benzoyl.

According to some of any of the embodiments described herein, the compound represented by Formula IIIa is prepared by:

converting D-ribose to a dioxolane-protected D-ribose;
oxidizing a hydroxy group at position 5" to a respective aldehyde; and
reacting the aldehyde with N-Benzyl hydroxyl amine hydrochloride.

According to some of any of the embodiments described herein, D is an N-benzyloxycarbonyl (CBz)-protected amino group, $R_8$ is methyl, and each of $T_1$ and $T_2$ is benzoyl, the process being essentially as described herein and depicted in FIG. 1.

According to some of any of the embodiments described herein, preparing the compound represented by Formula IIIa from D-ribose, reacting the compound represented by Formula IIIa with the Grignard reagent, converting the compound represented by Formula IIIb to the compound represented by Formula IIIc and reacting the compound represented by Formula IIIc with an amino-protecting group to thereby form the D, are performed as a "one pot reaction".

According to an aspect of some embodiments of the present invention there is provided a process of preparing a pseudo-trisaccharide aminoglycoside compound represented by Formula I:

Formula I

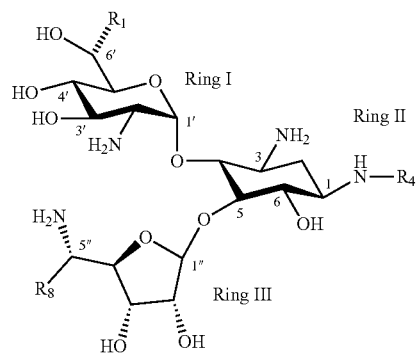

or a pharmaceutically acceptable salt thereof,
wherein:
the (rectangular) dashed line represents an S-configuration or an R-configuration at position 6';
$R_1$ is selected from hydrogen, alkyl, cycloalkyl or aryl;
$R_4$ is selected from hydrogen, acyl, and an amino-substituted alpha-hydroxy acyl; and
$R_8$ is alkyl, preferably methyl,
the process comprising:
preparing a compound represented by Formula III, according to any one of the respective embodiments and any combination thereof; and
coupling the compound represented by Formula III with a compound represented by Formula II:

Formula II

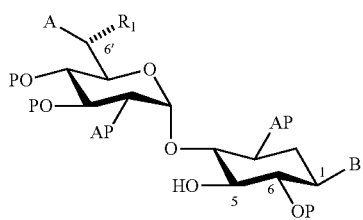

wherein:
the (rectangular) dashed line represents an S-configuration or an R-configuration at position 6';
OP is an acceptor-protected hydroxyl group;
AP is an acceptor-protected amino group;
A is an acceptor-protected hydroxyl group (OP); and
B is an acceptor-protected amine group, in case $R_4$ is Formula I is hydrogen, or a protected or unprotected form of a group defining $R_4$ when $R_4$ is other than hydrogen;
de-protecting the acceptor-protected and donor-protected hydroxyl groups;
de-protecting the acceptor-protected and donor-protected amino groups; and
de-protecting said protected form of a group defining $R_4$, if present,
thereby preparing a compound represented by Formula I.

According to some of any of the embodiments described herein, the coupling is effected in the presence of $BF_3$ etherate.

According to some of any of the embodiments described herein, the compound of Formula III is converted to an activated form thereof prior to the coupling.

According to some of any of the embodiments described herein, converting the compound of Formula III to the activated form is performed in situ, without isolating the activated form. According to some of any of the embodiments described herein, $R_1$ is methyl and $R_4$ is hydrogen and the compound represented by Formula II is prepared by:

converting G418 sulfate to 6-methyl paromamine;

converting hydroxyl groups to the acceptor-protected hydroxyl groups; and converting amino groups to the acceptor-protected amino groups.

According to some of any of the embodiments described herein, converting G418 sulfate to 6-methyl paromamine comprises contacting G418 in a form of a free base thereof with a methanolic solution of HCl.

According to some of any of the embodiments described herein, each of the acceptor-protected hydroxyl groups is O-acetyl.

According to some of any of the embodiments described herein, de-protecting the acceptor-protected hydroxyl groups is effected in a methanolic ammonia solution.

According to some of any of the embodiments described herein, each of the acceptor-protected amino groups is an N-benzyloxycarbonyl (CBz)-protected amino group.

According to some of any of the embodiments described herein, de-protecting the acceptor-protected amino groups is effected by Pd/C-catalyzed hydrogenation.

According to some of any of the embodiments described herein, a stereoconfiguration at position 6' is an R-configuration.

According to some of any of the embodiments described herein, the compound of Formula I is a sulfate salt, the process further comprising converting a compound represented by Formula I in a form of a free base thereof to the sulfate salt.

According to some of any of the embodiments described herein, the converting is performed by contacting a compound represented by Formula I in a form of a free base thereof with a methanolic solution of $H_2SO_4$.

Figure 2:
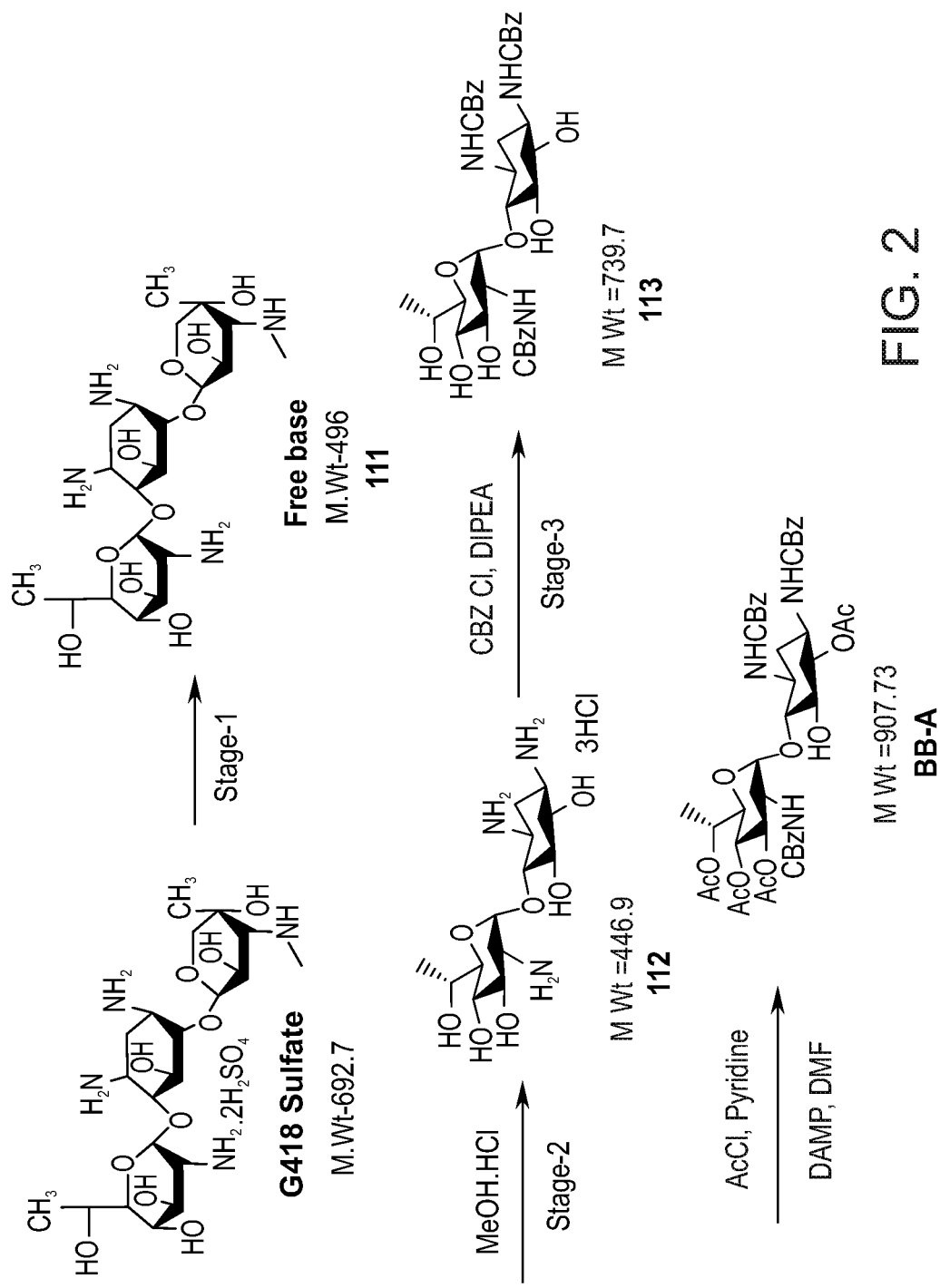
Figure 3:
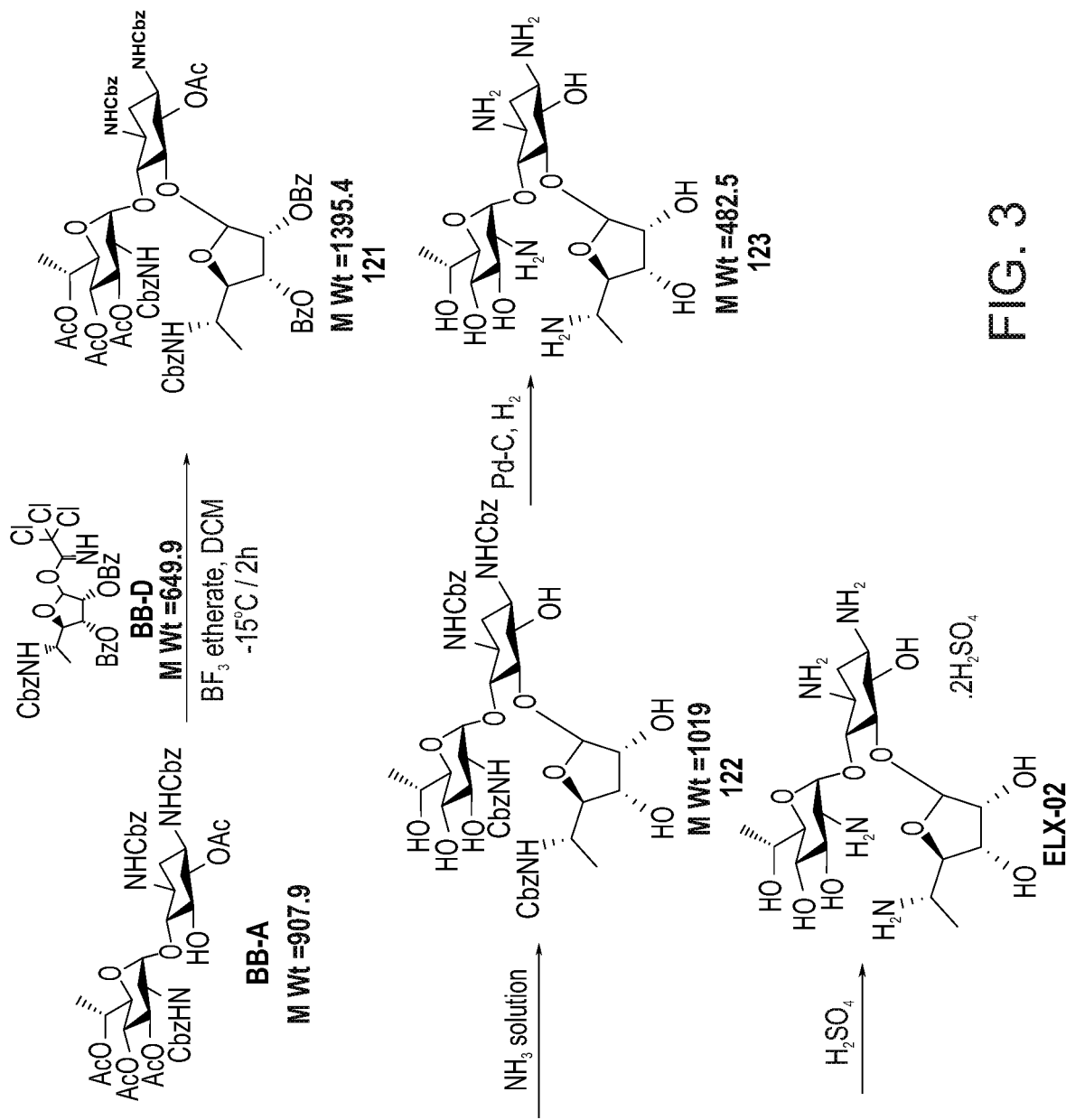

According to some of any of the embodiments described herein, $R_1$ is methyl, a configuration at position 6' is an R-configuration, $R_4$ is hydrogen, and $R_8$ is methyl. An exemplary such process is essentially as described herein and as depicted in FIGS. 1-3.

According to some of any of the embodiments described herein, the compound represented by Formula II is prepared as described in any one of the respective embodiments and any combination thereof.

According to an aspect of some embodiments of the present invention there is provided a process of preparing a compound represented by Formula II:

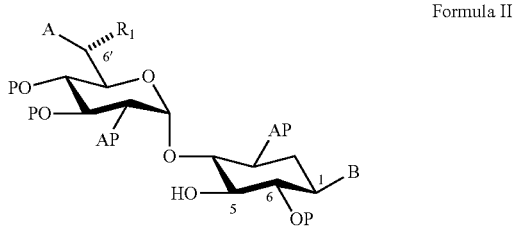

Formula II wherein:

the (rectangular) dashed line represents an S-configuration or an R-configuration at position 6';

$R_1$ is hydrogen, alkyl, cycloalkyl or aryl;

OP is an acceptor-protected hydroxyl group;

AP is an acceptor-protected amino group;

A is an acceptor-protected hydroxyl group (OP); and

B is an acceptor-protected amine group, an acyl, or a protected or unprotected amino-substituted alpha-hydroxy acyl, the process comprising:

providing a compound represented by Formula IIa:

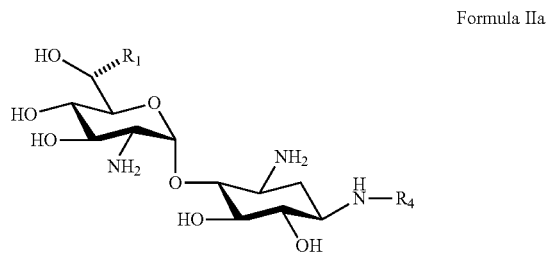

Formula IIa or a pharmaceutically acceptable salt thereof, wherein:

$R_4$ is hydrogen, acyl or an amino-substituted alpha-hydroxy acyl;

converting each of the amino groups to the acceptor-protected amino groups; and converting each of the hydroxy groups to the acceptor-protected hydroxyl groups.

According to some of any of the embodiments described herein, each of the acceptor-protected hydroxyl groups is O-acetyl.

According to some of any of the embodiments described herein, each of the acceptor-protected amino groups is an N-benzyloxycarbonyl (CBz)-protected amino group.

According to some of any of the embodiments described herein, $R_1$ is methyl, a configuration at position 6' is an R-configuration, and providing the compound of Formula IIa comprises converting G418 to the compound represented by Formula IIa.

According to some of any of the embodiments described herein, the converting comprises contacting G418 in a form of a free base thereof with a methanolic solution of HCl.

According to some of any of the embodiments described herein, $R_4$ is hydrogen, the process being essentially as described herein and depicted in FIG. 2.

According to an aspect of some embodiments of the present invention there is provided a process of stereoselectively preparing a compound represented by Formula IIIa, essentially as described herein.

According to an aspect of some embodiments of the present invention there is provided a process of preparing a compound represented by Formula IIIb, essentially as described herein.

According to an aspect of some embodiments of the present invention there is provided a process of preparing a compound represented by Formula IIIc, essentially as described herein.

According to an aspect of some embodiments of the present invention there is provided a pseudo-trisaccharide compound represented by Formula I, or a pharmaceutically acceptable salt thereof, prepared or obtainable by a process as described herein in any of the respective embodiments.

According to an aspect of some embodiments of the present invention there is provided a pharmaceutical composition comprising a pseudo-trisaccharide compound represented by Formula I as described and claimed herein and a pharmaceutically acceptable salt.

According to an aspect of some embodiments of the present invention there is provided a pseudo-trisaccharide compound represented by Formula I as described and claimed herein or a composition comprising same as described herein, for use in treating a genetic disorder.

According to an aspect of some embodiments of the present invention there is provided a compound represented by Formula III, prepared by the process as described herein in any of the respective embodiments.

According to an aspect of some embodiments of the present invention there is provided a compound represented by Formula IIIa.

According to an aspect of some embodiments of the present invention there is provided a compound represented by Formula IIIb.

According to an aspect of some embodiments of the present invention there is provided a compound represented by Formula IIIc.

According to an aspect of some embodiments of the present invention there is provided a process of preparing a pseudo-trisaccharide aminoglycoside compound represented by Formula Ia:

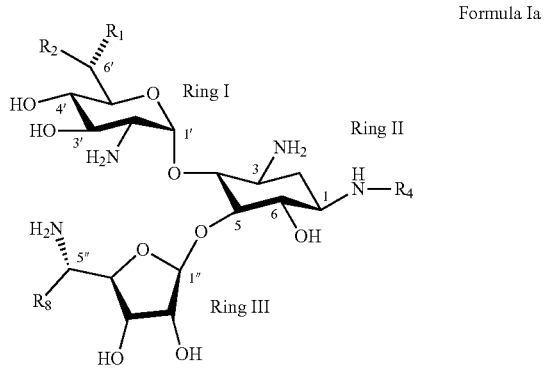

Formula Ia or a pharmaceutically acceptable salt thereof,
wherein:
the rectangular dashed line represents an S-configuration or an R-configuration at position 6';

$R_1$ is selected from hydrogen, alkyl, cycloalkyl or aryl;

$R_2$ is selected from a substituted or unsubstituted alkyl, OR' and NR'R", wherein each of R' and R" is independently selected from hydrogen, a substituted or unsubstituted alkyl, a substituted or unsubstituted cycloalkyl, a substituted or unsubstituted aryl, a substituted or unsubstituted heteroaryl, a substituted or unsubstituted alkaryl, and an acyl;

$R_4$ is selected from hydrogen, acyl, an amino-substituted alpha-hydroxy acyl, a substituted or unsubstituted alkyl, a substituted or unsubstituted cycloalkyl, a substituted or unsubstituted aryl, a substituted or unsubstituted alkaryl, and a cell-permealizable group; and $R_8$ is alkyl,
the process comprising:
preparing a compound represented by Formula III, according to the respective process as described herein in any of the respective embodiments and any combination thereof; and
coupling the compound represented by Formula III with a compound represented by Formula IIb:

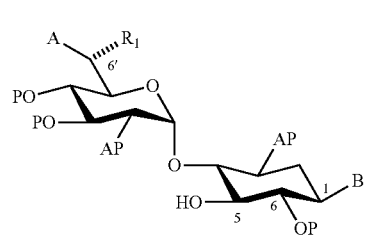

Formula IIb wherein:
the rectangular dashed line represents an S-configuration or an R-configuration at position 6';
OP is an acceptor-protected hydroxyl group;
AP is an acceptor-protected amino group;
A is an acceptor protected hydroxyl group (OP), when $R_2$ in Formula Ia is OR' and R' is hydrogen; an acceptor protected amine group (AP), when $R_2$ is Formula Ia is NR'R" and at least one of R' and R" is hydrogen; or is a protected or unprotected form of a group defining $R_2$ when $R_2$ is other than OH, $NH_2$, NHR' or NHR";
B is an acceptor-protected amine group (AP), when $R_4$ is Formula Ia is hydrogen, or a protected or unprotected form of a group defining $R_4$ when $R_4$ is other than hydrogen;
de-protecting the acceptor-protected and donor-protected hydroxyl groups;
de-protecting the acceptor-protected and donor-protected amino groups; and
de-protecting the protected form of a group defining $R_2$ and/or the protected from of a group defining $R_4$, if present,
thereby preparing a compound represented by Formula Ia.

According to some of any of the embodiments described herein, the coupling is effected in the presence of $BF_3$ etherate.

According to some of any of the embodiments described herein, the compound of Formula III is converted to an activated form thereof prior to the coupling.

According to some of any of the embodiments described herein, the converting the compound of Formula III to the activated form is performed in situ, without isolating the activated form.

According to some of any of the embodiments described herein, each of the acceptor-protected hydroxyl groups is O-acetyl.

According to some of any of the embodiments described herein, de-protecting the acceptor-protected hydroxyl groups is effected in a methanolic ammonia solution.

According to some of any of the embodiments described herein, each of the acceptor-protected amino groups is an N-benzyloxycarbonyl (CBz)-protected amino group.

According to some of any of the embodiments described herein, de-protecting the acceptor-protected amino groups is effected by Pd/C-catalyzed hydrogenation.

According to some of any of the embodiments described herein, a stereoconfiguration at position 6' is an R-configuration.

According to some of any of the embodiments described herein, the compound of Formula Ia is a sulfate salt, the process further comprising converting a compound represented by Formula Ia in a form of a free base thereof to the sulfate salt.

According to some of any of the embodiments described herein, the converting is performed by contacting a compound represented by Formula Ia in a form of a free base thereof with a methanolic solution of $H_2SO_4$.

According to an aspect of some embodiments of the present invention there is provided a pseudo-trisaccharide compound represented by Formula Ia, or a pharmaceutically acceptable salt thereof, prepared by the process according to any of the respective embodiments and any combination thereof.

According to an aspect of some embodiments of the present invention there is provided a pharmaceutical composition comprising the compound of Formula Ia as described herein and a pharmaceutically acceptable salt.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 4:
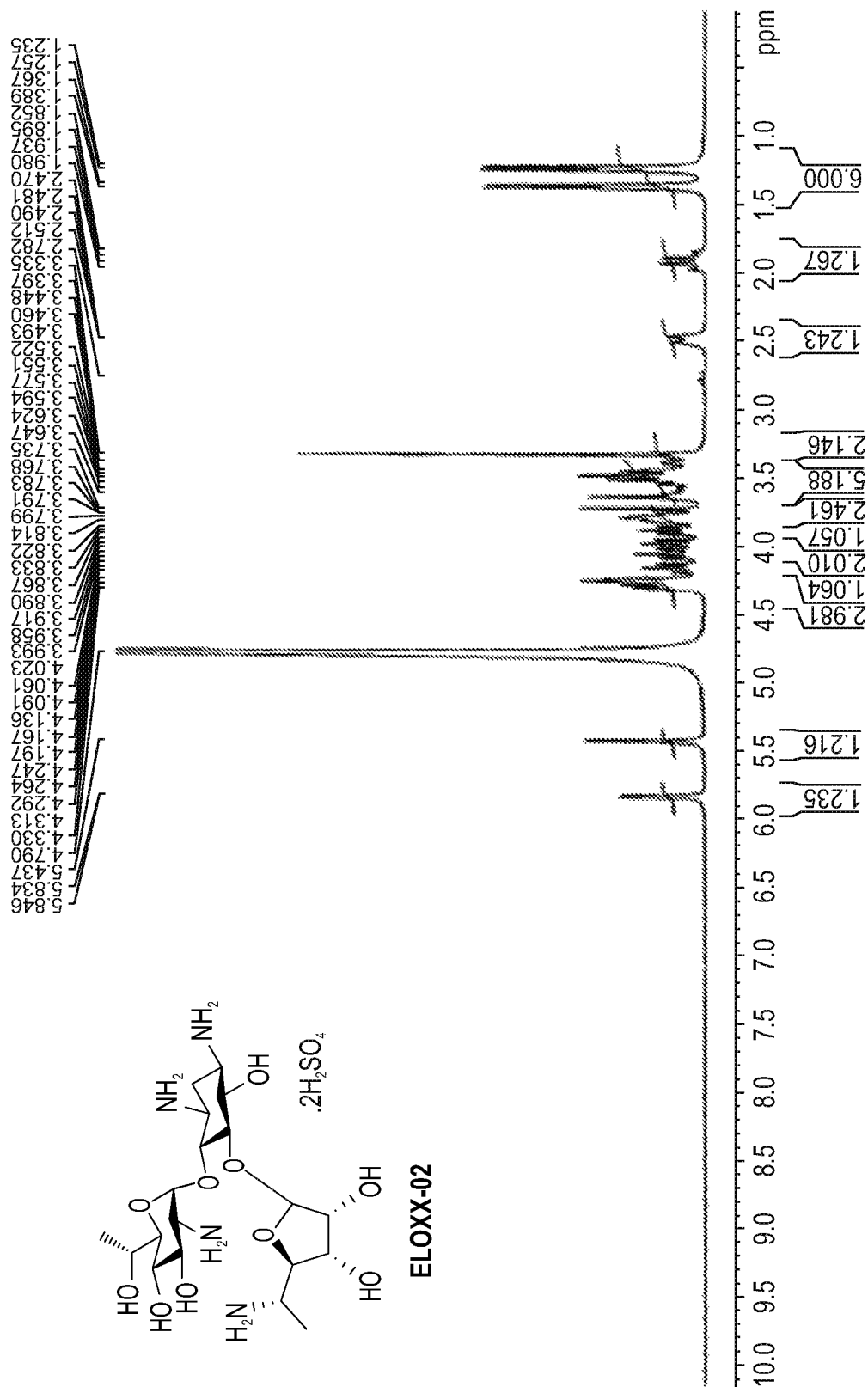
Figure 5:
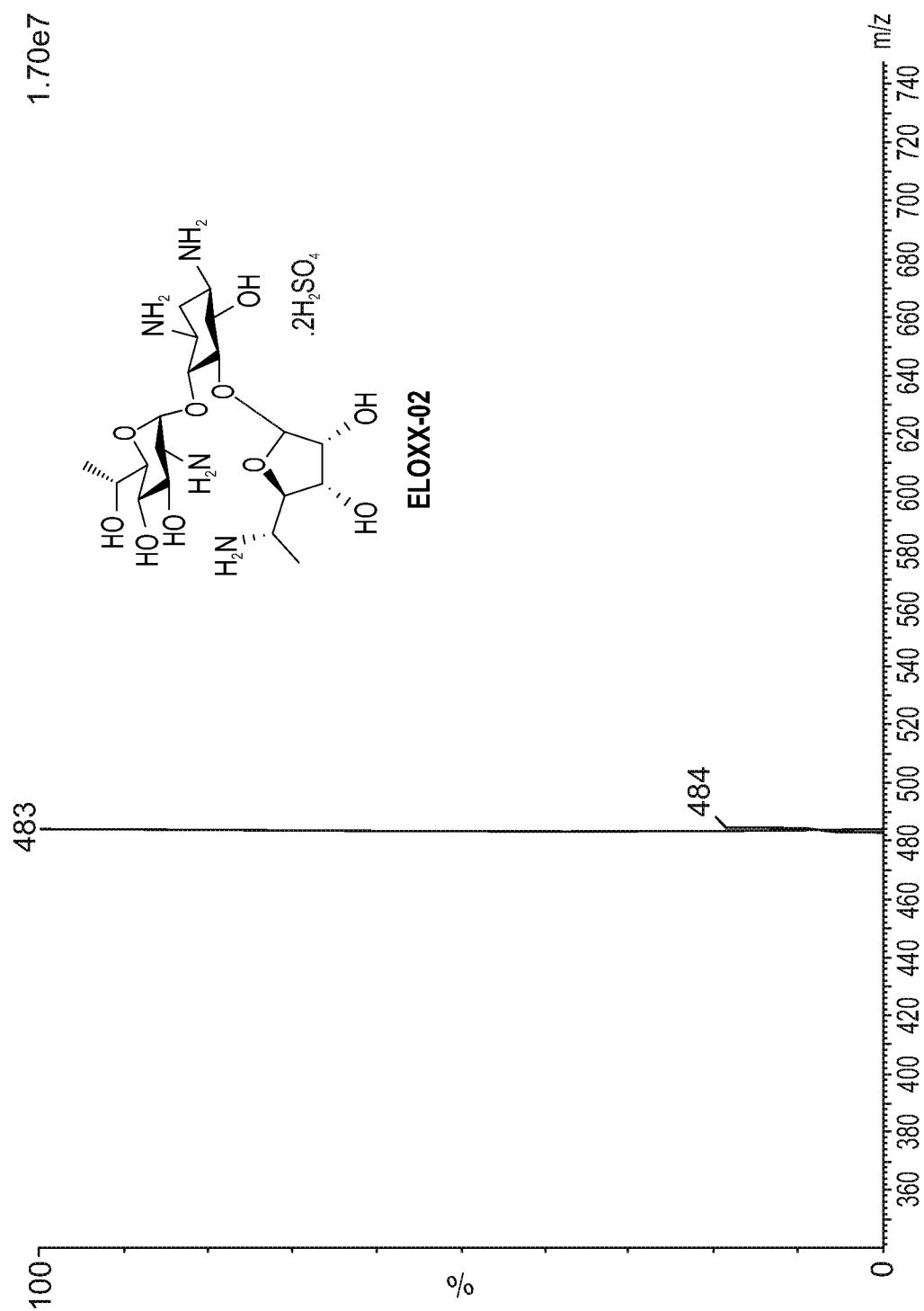

In the drawings:

FIG. 1 presents a schematic illustration of a synthetic pathway for preparing a monosaccharide donor, BB-D-OH, according to some embodiments of the present invention;

FIG. 2 presents a schematic illustration of a synthetic pathway for preparing a pseudo-disaccharide acceptor, BB-A, according to some embodiments of the present invention;

FIG. 3 presents a schematic illustration of a synthetic pathway for coupling BB-A and BB-D, hereby preparing the pseudo-trisaccharide ELX-02 (sulfate salt), according to some embodiments of the present invention;

FIG. 4 presents an $^1$H-NMR spectrum of ELX-02 (sulfate salt) prepared by the process depicted in FIG. 3;

FIG. 5 presents an Mass spectrum analysis of ELX-02 (sulfate salt) prepared by the process depicted in FIG. 3; and FIGS. 6A-B present the results of Rett Syndrome R270X nonsense mutation suppression dose-response cell-free assays conducted for ELX-02, at a concentration range of 0-12 μM, wherein FIG. 6A shows the expression level of the firefly luciferase, which is found downstream of the mutant sequence, as a fraction of the expression level exhibited in the control experiment (no added compound), and FIG. 6B shows the firefly/renilla expression ratio, down and upstream of the mutant sequence, as a fraction of the expression level in the control experiment;

DESCRIPTION OF SPECIFIC EMBODIMENTS OF THE INVENTION

The present invention, in some embodiments thereof, relates to synthesis of aminoglycosides and, more particularly, but not exclusively, to novel processes of preparing pseudo-trisaccharide aminoglycosides which exhibit readthrough activity and reduced toxicity, useful for large scale production of such aminoglycosides and of acceptor and donor intermediate compounds useful for preparing such aminoglycosides.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have designed and successfully practiced a novel process which is highly suitable for the large scale production of pseudo-trisaccharide aminoglycosides such as described in WO 2012/066546.

WO 2012/066546 describes pseudo-trisaccharide aminoglycoside compounds which exhibit readthrough activity, reduced toxicity to mammalian cells and reduced or even nullified antibacterial activity.

The pseudo-trisaccharide aminoglycoside compounds disclosed in WO 2012/066546 are prepared by coupling a donor monosaccharide compound with a pseudo-disaccharide acceptor derived from paromomycin, via a glycosylation reaction.

According to the teachings of WO 2012/066546, the donor compound is prepared as depicted in background art Scheme 1, using the thioglycoside Compound 7 as a starting material:

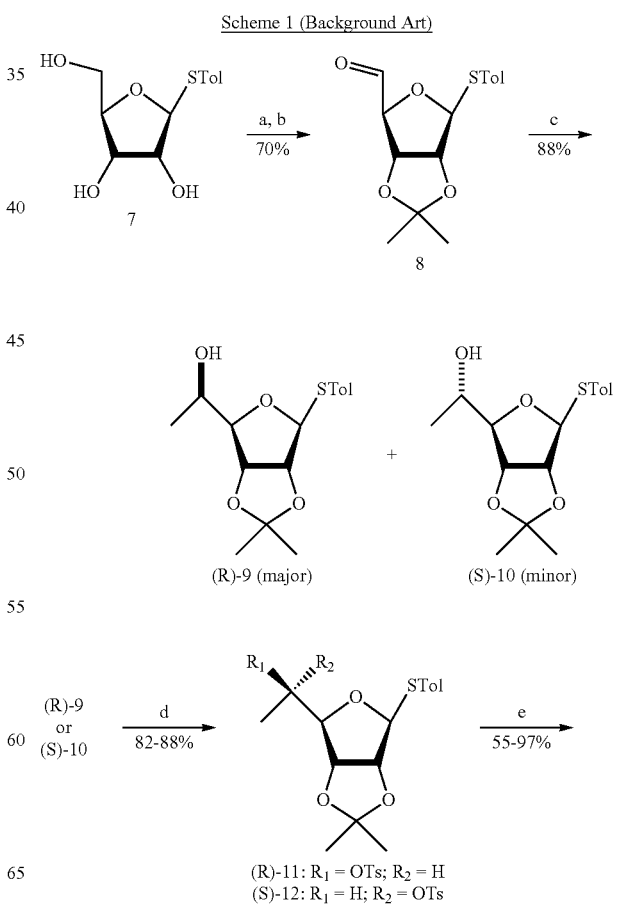

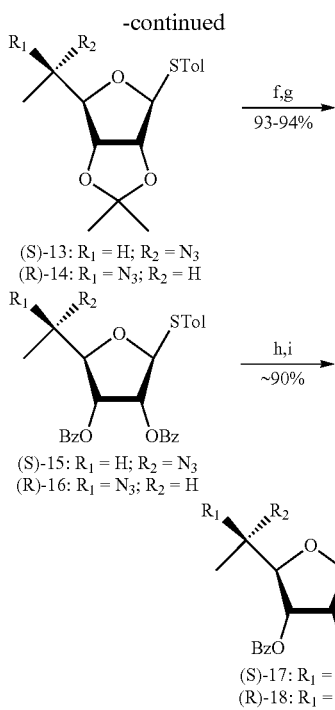

(S)-13: $R_1 = H; R_2 = N_3$
(R)-14: $R_1 = N_3; R_2 = H$ (S)-15: $R_1 = H; R_2 = N_3$
(R)-16: $R_1 = N_3; R_2 = H$ (S)-17: $R_1 = H; R_2 = N_3$
(R)-18: $R_1 = N_3; R_2 = H$ wherein "a" represents 1,1-dimethoxypropane, CSA, acetone, room temperature; "b" represents Dess-Martin periodinane (DMP), DCM, room temperature; "c" represents MeMgBr, THF, −30° C.; "d" represents TsCl, Py, 4-DMAP, room temperature; "e" represents $NaN_3$, HMPA, DMF, 70° C.; "f" represents acetic acid/water (8:2), reflux; "g" represents BzCl, Py, 4-DMAP, room temperature; "h" represents NBS, acetone/water (8:2), −30° C.; and "I" represents $CCl_3CN$, DBU, DCM, 0° C.).

Generally, according to the synthetic pathway disclosed in WO 2012/066546, selective protection of C2- and C3-hydroxyls by isopropylidine (2,2-dimethoxy propane/acetone, CSA) was followed by oxidation of the remaining primary alcohol using Dess-Martin periodinane (DMP, dichloromethane) to afford the aldehyde Compound 8 in 70% isolated yield for two steps. Treatment of Compound 8 with MeMgBr gave the corresponding secondary alcohol as a mixture of C5-diastereomers (4:1 ratio) in 88% isolated yield. The major and minor diastereomers exhibit (R)- and (S)-configuration, respectively (Compounds (R)-9 and (S)-10).

This mixture was separated by flash column chromatography.

The following steps in Background Art Scheme 1 were separately performed on each diastereomer. Tosylation (TsCl, pyridine, 4-DMAP) of the secondary alcohol was followed by $S_N2$ displacement of the corresponding tosylates (Compounds (R)-11 and (S)-12) with $NaN_3$ (DMF, HMPA) to furnish the azides Compounds (S)-13 and (R)-14 with inverted configurations. Hydrolysis of the isopropylidene ketal with aqueous acetic acid, followed by benzoylation of the resulted secondary alcohols, provided the benzoates Compounds (S)-15 and (R)-16. The thioglycosides Compounds (S)-15 and (R)-16 were converted to the corresponding trichloroacetimidates Compounds (S)-17 and (R)-18 in two successive steps; hydrolysis with NBS in aqueous acetone and treatment of the resulted hemiacetals with $CCl_3CN$ in the presence of DBU. The donors Compounds (S)-17 and (R)-18 were used in glycosylation reactions without further purification.

According to the synthetic pathway disclosed in WO 2012/066546, Compound (S)-17 can be coupled to acceptor 219 to thereby generate pseudo-trisaccharide aminoglycoside compounds, as depicted in Background Art Scheme 2 below (corresponding to Scheme 4 of WO 2012/066546).

Scheme 2 (Background Art)

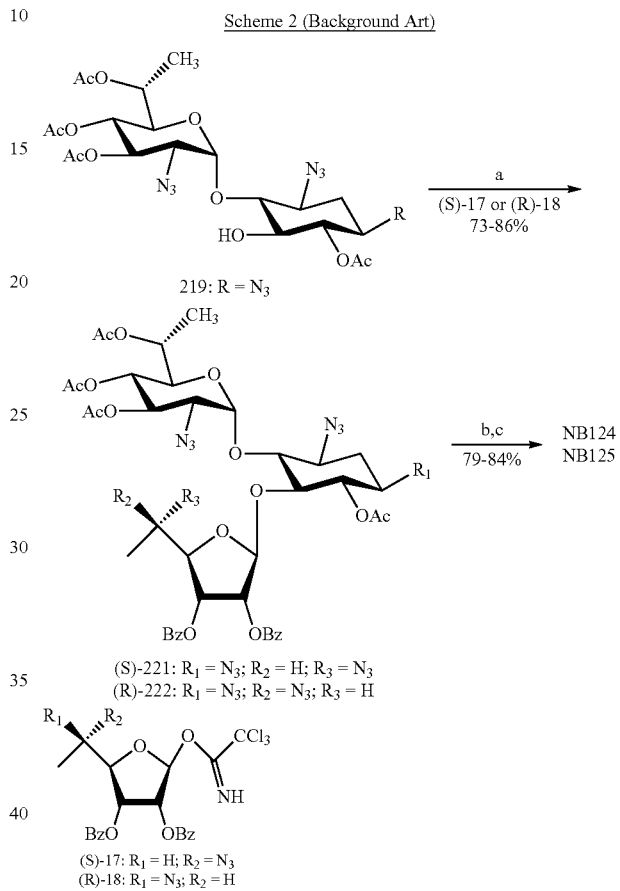

219: $R = N_3$ (S)-221: $R_1 = N_3; R_2 = H; R_3 = N_3$
(R)-222: $R_1 = N_3; R_2 = N_3; R_3 = H$ (S)-17: $R_1 = H; R_2 = N_3$
(R)-18: $R_1 = N_3; R_2 = H$ wherein "a" represents $BF_3.Et_2O$, DCM, 4 Å MS, −20° C.; "b" represents $MeNH_2.EtOH$, room temperature; and "c" represents $PMe_3$, NaOH, THF, room temperature.

The preparation of Acceptor 219 is described, for example, in Nudelman et al., 2010 (supra). Generally, G418 is hydrolyzed to obtain a pseudo-disaccharide 6-methyl paromamine core, which is then reacted with $TfN_3$ and acetic anhydride.

As further disclosed in WO 2012/066546, the "S" diastereomer NB124 is superior to the "R" enantiomer NB125.

In view of the promising therapeutic activity of Compound NB124, which is also referred to herein interchangeably as ELX-02 or ELOXX-02, extensive efforts have been conducted for improving its synthesis, for the purpose of devising a process suitable for large scale production of this compound.

In the initial studies conducted for scaling up the production of ELX-02, the general synthetic pathway which involves coupling of the donor (S)-17 to acceptor 219 (see, Background Art Scheme 2), and the synthetic pathways for preparing the donor and acceptor as previously described, were maintained. The respective procedure for preparing ELX-02 resulted in a 17-step synthesis, and involved numerous chromatographic separations, although some chromatographic separations were replaced by crystallization procedures, and the amount of the donor was substantially reduced (e.g., from 4 mol equivalents to 2 mol equivalents). Notably, while following the synthetic pathway disclosed in WO 2012/066546 for preparing the donor molecule, a chromatographic separation of the (R) and (S) stereoisomers is required (see, Background Art Scheme 1).

In a search for a further improved synthetic pathway, the present inventors have devised a novel process for preparing the desired S-stereoisomer of the donor molecule, which is referred to herein as Compound (S)-17, and interchangeably as BB-D-OH. This newly designed process involves a stereoselective synthesis of the desired stereoisomer of the donor, thereby circumventing the need to perform the laborious, costly and less effective chromatographic separation of the stereoisomers.

The synthesis of BB-D-OH, which is described in further detail in the Examples section that follows, and is depicted in FIG. 1, uses D-Ribose as the starting material. Generally, D-Ribose is protected with acetone in methanol to give 1-methoxy acetonide, which is oxidized to the corresponding aldehyde. Reaction of this aldehyde with benzylhydroxylamine leads to formation of nitrone, which is then reacted stereoselectively with a Grignard reagent such as methylmagnesium chloride to thereby yield the protected intermediate as a single desired (S) stereoisomer. Deprotection of the protecting groups gives 5-amino-5,6-dideoxy-2,3-dihydroxy-1-methoxy-alpha-L-talofuranoside, which is then re-protected by CBz chloride to form an N-CBz-derivative, which is a solid compound that is separated and purified by crystallization. This 7-steps synthesis can be performed as a "one-pot" synthesis without separation and purification of intermediates, with 26-28% overall yield (85-90% yield of each step), thus representing an actual one-step synthesis in terms of industrial processes. The obtained 2,3-dihydroxy intermediate is thereafter protected by benzoyl chloride (77-78% yield), followed by deprotection of the methoxy group (53-57% yield). The resulting 1-hydroxy compound is converted to BB-D-OH in almost quantitative yield.

This synthetic pathway of preparing BB-D-OH represents an actual 4-step industrial synthesis, and involves a single chromatographic purification procedure.

Compared to the synthetic pathway described in WO 2012/066546, the overall number of synthetic steps and, importantly, the overall number of chromatographic purification procedures, is substantially reduced, in addition to the circumvention of a chromatic separation of stereoisomers, rendering this process highly suitable for large-scale production of this donor compound and of the final pseudo-trisaccharide compound prepared by coupling it to a suitable acceptor molecule.

In order to further improve the production of ELX-02 and similar pseudo-trisaccharide aminoglycosides such as described in WO 2012/066546, the present inventors have designed and successfully practiced also novel synthetic pathways for preparing the acceptor 219 (see, Background Art Scheme 2), which is also referred to herein interchangeably as BB-A, for coupling the donor BB-D-OH, or an activated form thereof denoted herein as BB-D, to acceptor BB-A, and for the salt formation of the final product ELX-02 as a sulfate salt.

The synthesis of BB-A, which is described in further detail in the Examples section that follows, and is depicted in FIG. 2, uses G418 sulfate (also referred to herein and in the art simply as G418) as the starting material. G418 is hydrolyzed using a hydrogen chloride solution in methanol. This newly used reagent provides a better conversion and yield of the desired 6-methylparomamine.

The protection of the amino groups of the paromamine core is performed using CBz group, instead of the previously described azide group which is obtained using triflic anhydride and the hazardous sodium azide. The CBz-protected 6-methylparomamine is prepared and used at the next step without chromatographic purification. In the next step, hydroxy groups are protected by acetylation, using acetyl chloride and using pyridine as a base, and therefore in a substantially reduced amount compared to previous synthetic pathways in which pyridine is used as a solvent. This modification further results in increased yield of this step, from the previously reported 60% to 73-78%.

CBz and Ac groups were selected as protecting groups due to their compatibility with the protecting groups (CBz, Bz) in BB-D.

The coupling reaction between the donor BB-D or BB-D-OH and Acceptor BB-A, which is described in further detail in the Examples section that follows, and is depicted in FIG. 3, is performed using a substantially reduced amount of BB-D (1.5 mol equivalent of BB-D to 1 mol of BB-A). The following deacetylation is performed using an ammonia solution in methanol instead of the expensive, previously used methylamine in ethanol. Deprotection of CBz-group is performed using hydrogenation instead of the hazardous and expensive trimethylphosphine deprotection of the azide group.

Overall, the newly designed acceptor, the process of its preparation and the coupling processes described herein utilize protecting groups which allow performing the coupling and deprotection reactions in good yields, while avoiding the use of hazardous and/or expensive chemical reagents.

As described in WO 2012/066546, NB124 is used as its sulfate salt form, and was converted to this salt using aqueous sulfuric acid. In the process described herein, methanolic sulfuric acid is used, rendering salt formation and precipitation substantially more efficient.

Some embodiments of the present invention therefore relate to a novel process of preparing BB-D-OH, to a novel process of coupling BB-D-OH, optionally in its activated form BB-D, to a suitable acceptor to thereby obtain a pseudo-trisaccharide aminoglycoside compound such as described in WO 2012/066546, to a novel process of preparing an acceptor BB-A as described herein, and to a novel process of coupling BB-A and BB-D-OH (or BB-D) and generating the final pseudo-trisaccharide aminoglycoside thereupon.

The donor described herein as BB-D-OH, and the process of its preparation can be coupled to other mono-, di- and tri-saccharide or pseudo-saccharide acceptors, and thus can be utilized in processes of preparing pseudo-disaccharide, pseudo-trisaccharide, pseudo-tetrasaccharide aminoglycosides. In some embodiments of the present invention, the donor described herein is utilized in the preparation of pseudo-trisaccharide aminoglycoside compound such as described in WO 2017/037718.

In some embodiments of the present invention, the synthetic pathways described herein for preparing acceptor molecules such as BB-A, for coupling the donor to the acceptor, and for the salt formation of the final product as a sulfate salt, are utilized in processes of preparing pseudo-trisaccharide aminoglycoside compound such as described in WO 2017/037718. Herein, the term "stereoisomers" encompasses enantiomers and diastereomers.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems. In the context of the present embodiments, a compound may exhibit one or more chiral centers, each of which exhibiting an R- or an S-configuration and any combination, and compounds according to some embodiments of the present invention, can have any one of their chiral centers exhibit an R- or an S-configuration, unless otherwise indicated.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers. Each stereo-center (chiral center) gives rise to two different configurations and thus to two different stereoisomers. In the context of the present invention, some embodiments of the present invention encompass compounds with multiple chiral centers that occur in any combination of stereo-configuration, namely any diastereomer. Some embodiments of the present invention relate to compounds with multiple chiral centers, each of which exhibits exhibit an R- or an S-configuration, as described and depicted herein, unless otherwise indicated.

In the structural formulae presented herein throughout, whenever a chiral carbon features a defined R- or an S-configuration, its chirality is represented by a triangle dashed or bolded line, as acceptable in the art, depending on the indicated stereoconfiguration, and is not specified. Whenever a chiral carbon features a configuration that can be either R-configuration or S-configuration, it is represented by a rectangular dashed line and is described as such. Chiral carbon atoms which can adopt R-configuration or S-configuration or a racemic mixture thereof are presented herein by a simple line or a curved (wavy) line.

The term "acceptor" is used herein to describe a skeletal structure derived from paromamine which has an available (unprotected) hydroxyl group at position C5, which is reactive during a glycosylation reaction, and can accept a glycosyl.

The term "donor" is used herein to describe a glycosyl that reacts with the acceptor to form the final pseudo-trisaccharide compound.

The term "glycosyl", as used herein, refers to a chemical group which is obtained by removing the hydroxyl group from the hemiacetal function of a monosaccharide.

The term "monosaccharide", as used herein and is well known in the art, refers to a simple form of a sugar that consists of a single saccharide molecule which cannot be further decomposed by hydrolysis. The monosaccharide according to embodiments of the present invention is a ribose. When classified according to the number of carbon atoms of the carbohydrate, the monosaccharide is a pentose, having 5 carbon atoms.

The donors and acceptors are designed so as to form the desired pseudo-trisaccharide aminoglycoside compounds according to some embodiments of the present invention.

The syntheses of the compounds according to some embodiments of the present invention, generally include (i) preparing an acceptor compound by selective protection of one or more hydroxyls and amines at selected positions present on the paromamine scaffold, leaving the selected position (C5) unprotected and therefore free to accept a donor (glycosyl) compound as defined herein; (ii) preparing a desired stereoisomer of a donor compound by, inter alia, selective protection of one or more hydroxyls and amines at selected positions present on the glycosyl, leaving one position unprotected and therefore free to couple with an acceptor compound as defined herein; (iii) subjecting the donor and the acceptor to a coupling reaction; and (iii) removing the protecting groups to thereby obtain the desired compound.

The phrase "protected group", as used herein, refers to a group that is substituted or modified so as to block its functionality and protect it from reacting with other groups under the reaction conditions (e.g., a coupling reaction as described herein). A protected group is re-generated by removal of the substituent or by being re-modified.

When an "amino-protected group" or "hydroxyl-protected group" are used, it is meant that a protecting group is attached or used to modify the respective amine or hydroxy group so as to generate the indicated protected group.

The phrase "protecting group", as used herein, refers to a substituent or a modification that is commonly employed to block or protect a particular functionality while reacting other functional groups on the compound. The protecting group is selected so as to release the substituent or to be re-modified, to thereby generate the desired unprotected group.

For example, an "amino-protecting group" or "amine-protecting group" is a substituent attached to an amino group, or a modification of an amino group, that blocks or protects the amino functionality in the compound, and prevents it from participating in chemical reactions.

The amino-protecting group is removed by removal of the substituent or by a modification that re-generates an amine group.

An exemplary amino-protected group usable according to some embodiments of the present invention is N-benzyloxycarbonyl (CBz).

A "hydroxyl-protecting group" or "hydroxy-protecting group" refers to a substituent or a modification of a hydroxyl (hydroxy) group that blocks or protects the hydroxyl functionality, and prevents it from participating in chemical reactions. The hydroxy-protecting group is removed by removal of the substituent or by a modification that re-generates a hydroxy group.

Suitable hydroxy protected groups include isopropylidene ketal and cyclohexanone dimethyl ketal (forming a 1,3-dioxane with two adjacent hydroxyl groups), 4-methoxy-1-methylbenzene (forming a 1,3-dioxane with two adjacent hydroxyl groups), O-acetyl, O-chloroacetyl, O-benzoyl and O-silyl.

For a general description of protecting groups and their use, see T. W. Greene, Protective Groups in Organic Synthesis, John Wiley & Sons, New York, 1991.

According to some embodiments, exemplary hydroxy-protected groups include O-acetyl (AcO-) and O-benzoyl.

It is noted herein that when applicable, a "protected group" refers to a moiety in which one reactive function on a compound is protected or more than one function are protected at the same time, such as in the case of two adjacent functionalities, e.g., two hydroxyl groups that can be protected at once by forming a ketal, e.g., isopropylidene ketal.

The Pseudo-Trisaccharide Aminoglycoside Compounds:

The processes as described herein are useful for a large-scale production (e.g., as described herein) of pseudo-trisaccharide aminoglycoside compounds such as those represented by Formula I:

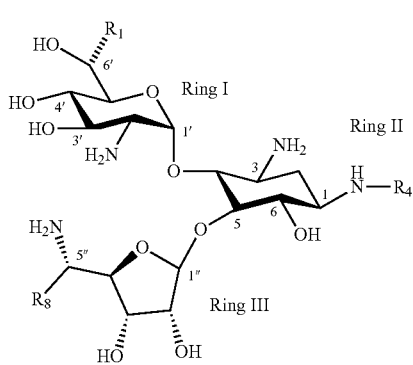

Formula I wherein:

the (rectangular) dashed line represents an S-configuration or an R-configuration at position 6', preferably as R-configuration;

$R_1$ is selected from hydrogen, alkyl, cycloalkyl or aryl, and is preferably alkyl, more preferably methyl;

$R_4$ is selected from hydrogen, acyl, and an amino-substituted alpha-hydroxy acyl, and is preferably hydrogen; and $R_8$ is selected from alkyl, cycloalkyl or aryl, and is preferably alkyl, more preferably methyl.

Representative compounds are described in WO 2012/066546.

The compounds represented by Formula I can be in a form of a free base or in a form of a salt thereof, preferably a pharmaceutically acceptable salt thereof.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound. A pharmaceutically acceptable salt of a compound as described herein can alternatively be formed during the synthesis of the compound, e.g., in the course of isolating the compound from a reaction mixture or re-crystallizing the compound.

In the context of some of the present embodiments, a pharmaceutically acceptable salt of the compounds described herein may optionally be an acid addition salt comprising at least one basic (e.g., amine and/or guanidine) group of the compound which is in a positively charged form (e.g., wherein the basic group is protonated), in combination with at least one counter-ion, derived from the selected base, that forms a pharmaceutically acceptable salt.

The acid addition salts of the compounds described herein may therefore be complexes formed between one or more basic groups of the compound and one or more equivalents of an acid.

Depending on the stoichiometric proportions between the charged group(s) in the compound and the counter-ion in the salt, the acid additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

An example, without limitation, of a pharmaceutically acceptable salt would be an ammonium cation and an acid addition salt thereof.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

The present embodiments further encompass any prodrugs, solvates, and/or hydrates of the compounds described herein.

An exemplary compound represented by Formula I according to some embodiments of the present invention is NB124, which is also referred to herein as ELX-02, or a pharmaceutically acceptable salt thereof, for example, a sulfuric acid addition salt thereof (e.g., a di-addition salt).

The processes as described herein are useful for a large-scale production (e.g., as described herein) of pseudo-trisaccharide aminoglycoside compounds such as those represented by Formula Ia:

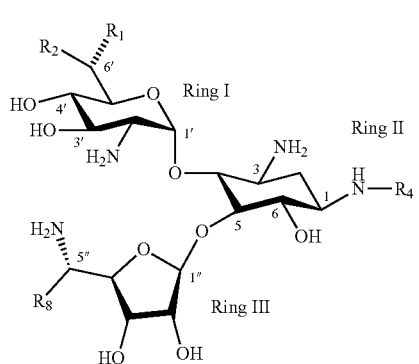

Formula I or a pharmaceutically acceptable salt thereof, as described herein.

wherein:
the rectangular dashed line indicates a stereo-configuration of position 6' being an R configuration or an S configuration;

$R_1$ is selected from hydrogen, alkyl, cycloalkyl or aryl;

$R_2$ is selected from a substituted or unsubstituted alkyl, OR' and NR'R", wherein each of R' and R" is independently selected from hydrogen, a substituted or unsubstituted alkyl, a substituted or unsubstituted cycloalkyl, a substituted or unsubstituted aryl, a substituted or unsubstituted heteroaryl, a substituted or unsubstituted alkaryl, and an acyl;

$R_4$ is selected from hydrogen, acyl, an amino-substituted alpha-hydroxy acyl, a substituted or unsubstituted alkyl, a substituted or unsubstituted cycloalkyl, a substituted or unsubstituted aryl, a substituted or unsubstituted alkaryl, and a cell-permealizable group, as described herein; and $R_8$ is alkyl, as described herein.

According to some embodiments of the present invention, the amine substituent at position 1 of the aminoglycoside structure is modified, such that $R_4$ is other than hydrogen.

Herein throughout, an amine which bears a substituent other than hydrogen is referred to herein as a "modified amine substituent" or simply as a "modified amine".

According to some embodiments of the present invention, the amine substituent at positions 1 of the aminoglycoside structure is modified to include a hydrophobic moiety such as alkyl, cycloalkyl, alkaryl and/or aryl, or a group which is positively-charged at physiological pH and which can increase cell permeability of the compound (also referred to herein interchangeably as "cell-permealizable group" or "cell-permealizing group"), such as guanine or guanidine groups, as defined herein, or, alternatively, hydrazine, hidrazide, thiohydrazide, urea and thiourea.

In some of any of the embodiments described herein, $R_1$ is alkyl, and in some embodiments it is a lower alkyl, of 1 to 4 carbon atoms, including, but not limited to, methyl, ethyl, propyl, butyl, isopropyl, and isobutyl.

In some of any of the embodiments described herein, $R_1$ is a non-substituted (unsubstituted) alkyl.

In some of any of the embodiments described herein, $R_1$ is methyl.

Alternatively, in some of any of the embodiments described herein, $R_1$ is cycloalkyl, including, but not limited to, cyclopropyl, cyclobutyl, cyclopentyl and cyclohexyl.

Further alternatively, in some of any of the embodiments described herein, $R_1$ is aryl, such as a substituted or unsubstituted phenyl. Non-limiting examples include unsubstituted phenyl and toluene.

Further alternatively, in some of any of the embodiments described herein, $R_1$ is alkaryl, such as a substituted or unsubstituted benzyl.

In some of any of the embodiments described herein, $R_1$ is alkyl. In some embodiments, $R_1$ is methyl.

In some of any of the embodiments described herein $R_2$ is OR'.

In some of these embodiments, R' is hydrogen, and $R_2$ is hydroxy.

In other embodiments, $R_2$ is OR' and R' is other than hydrogen.

In some of these embodiments, R' is a substituted or unsubstituted alkyl, as defined herein, or a substituted or unsubstituted cycloalkyl, as defined herein, and $R_2$ is alkoxy.

In some of these embodiments, R' is a substituted or unsubstituted aryl, as defined herein, and $R_2$ is aryloxy.

In some of these embodiments, R' is acyl, as defined herein, and $R_2$ is carboxylate, as defined herein.

Alternatively, $R_2$ is NR'R".

In some of these embodiments, R' and R" are both hydrogen.

In some of these embodiments, one or both of R' and R" is other than hydrogen.

Exemplary chemical groups which can be represented by variable $R_2$ in Formula Ia, when $R_2$ is NR'R", include, but are not limited to, compounds in which R' is hydrogen and R" is alkyl amino, such as NH—$(CH_2)$n-$NH_2$, with n being, for example, from 1 to 6; compounds in which R' is hydrogen and R" is NH—$(CH_2)$n-OH, with n being, for example, from 1 to 6; compounds in which R' is hydrogen and R" is NH—$(CH_2)$n-C(=O)R''', with n being, for example, from 1 to 6, and R''' being hydrogen or alkyl or cycloalkyl or aryl; compounds in which R' is hydrogen and R" is NH—$(CH_2)$n-CH(OR')$_2$, with n being, for example, from 1 to 6, and R''' being hydrogen or alkyl or cycloalkyl or aryl; and compounds in which R' is hydrogen and R" is NH—$(CH_2)$n-R''', with n being, for example, from 1 to 6, and R''' being hydrogen or alkyl or cycloalkyl or aryl or heteroaryl or heteroalicyclic.

In some of any of the embodiments described herein, $R_2$ is alkyl, and in some of these embodiments $R_2$ is a substituted alkyl, for example, an alkyl substituted by one or more amine groups (aminoalkyl).

In some of any of the embodiments described herein, and any combination thereof, the amine substituent at position 1 (Ring II) in Formula Ia, is a modified amine, as described herein, such that $R_4$ is other than hydrogen.

In some of these embodiments, $R_4$ can be alkyl, alkaryl, cycloalkyl, aryl, an acyl, or an amino-substituted α-hydroxy acyl, as defined herein, such as, for example, (S)-4-amino-2-hydroxybutyryl (AHB), or (S)-4-amino-2-hydroxypropionyl (AHP).

In some of the embodiments where $R_4$ is alkyl, the alkyl can be, for example, a lower alkyl, of 1-4 carbon atoms, such as, but not limited to, methyl, ethyl, propyl, butyl, isopropyl, and isobutyl, each being optionally substituted, as described herein.

In some of these embodiments, the alkyl is independently a non-substituted alkyl, such as, but not limited to, ethyl, propyl and isopropyl.

In some of these embodiments, the alkyl is independently a substituted methyl, such as, but not limited to, an alkaryl such as benzyl.

Alternatively, $R_4$ is cycloalkyl, and the cycloalkyl can be, for example, cyclopropyl, cyclobutyl, cyclopentyl and cyclohexyl.

Further alternatively, $R_4$ is aryl, and the aryl can be, for example, a substituted or unsubstituted phenyl. Non-limiting examples include unsubstituted phenyl and toluene.

In some of any of the embodiments described herein, $R_4$ is alkyl, cycloalkyl or aryl, as described herein.

In some of these embodiments, $R_1$ is alkyl, cycloalkyl or aryl, and is preferably alkyl, as defined herein.

In some of any of the embodiments described herein, $R_4$ is alkyl and in some embodiments it is a lower alkyl, of 1-4 carbon atoms.

In some embodiments, $R_4$ is an alkyl such as ethyl, propyl, butyl, isopropyl, isobutyl, tert-butyl, each being optionally substituted.

In some embodiments, $R_4$ is methyl or ethyl, and is preferably a substituted methyl or ethyl. In some of these embodiments, the methyl or ethyl is substituted by, for example, a cycloalkyl or aryl. Such substituents are also referred to in the art as alkylcycloalkyl and alkaryl, respectively. An exemplary alkaryl is benzyl (—CH$_2$-Phenyl).

In some embodiments, R$_4$ is propyl or isopropyl.

In some embodiments, R$_4$ is benzyl.

In some of any of the embodiments described herein, R$_4$ is a cell-permealizable group, as defined herein, and in some embodiments, R$_4$ is guanidinyl.

In some of any of the embodiments described herein, R$_1$ is alkyl, cycloalkyl or aryl, and is preferably alkyl, as defined herein, and R$_4$ is alkyl, as defined herein, preferably, ethyl, propyl, isopropyl or benzyl.

In some of any of the embodiments described herein, R$_1$ is alkyl, cycloalkyl or aryl, and is preferably alkyl, as defined herein; and R$_4$ is a cell-permealizing group, as defined herein, preferably, guanidine or guanine.

Herein, a cell-permealizable group, which is also referred to herein interchangeably as "cell-permealizing group" encompasses a group which is typically positively-charged at physiological pH and which can increase cell permeability of the compound. Examples include, without limitation, guanine or guanidine groups, as defined herein, or, alternatively, hydrazine, hidrazide, thiohydrazide, urea and thiourea, as defined herein.

In some of any of the embodiments described herein, R$_1$ is alkyl, cycloalkyl or aryl, and is preferably alkyl, as defined herein; and R$_4$ is a cell-permealizing group, as defined herein, preferably, guanidine or guanine, more preferably guanidine.

In some of any of the embodiments described herein, R$_4$ is hydrogen or a moiety such as (S)-4-amino-2-hydroxybutyryl (AHB), or (S)-4-amino-2-hydroxypropionyl (AHP).

In some of any of the embodiments described herein, R$_1$ is alkyl, cycloalkyl or aryl, and is preferably alkyl, as defined herein; R$_4$ is hydrogen or amino-substituted α-hydroxy-acyl, as defined herein; and R$_5$ is a guanidine group (guanidinyl).

In some of any one of the embodiments described herein for Formula Ia, and any combination thereof, the configuration at position 6' is an R-stereoconfiguration.

In some of any one of the embodiments described herein for Formula Ia, and any combination thereof, the configuration at position 5" is an S-stereoconfiguration.

Herein throughout, the term "acyl" describes a —C(=O)—R group, with R being a substituted or unsubstituted alkyl, cycloalkyl, aryl, alkaryl, or hydrogen.

In exemplary embodiments, the acyl is such that R is an alkyl or alkaryl or aryl, each of which being optionally substituted by one or more amine substituents.

In some embodiments, the R is a substituted alkyl, and in some embodiments, R is substituted by hydroxy at the α position with respect to the carbonyl group, such that the acyl is α-hydroxy-acyl.

In some embodiments, the α-hydroxy-acyl is further substituted by one or more amine groups, and is an amino-substituted α-hydroxy-acyl.

In some of the embodiments of an acyl group as described herein, the amine substituents can be, for example, at one or more of positions β, γ, δ, and/or ω of the moiety R, with respect to the acyl.

Exemplary amino-substituted α-hydroxy-acyls include, without limitation, the moiety (S)-4-amino-2-hydroxybutyryl, which is also referred to herein as AHB. According to some embodiments of the present invention, an alternative to the AHB moiety can be the α-hydroxy-β-aminopropionyl (AHP) moiety. Additional exemplary amino-substituted α-hydroxy-acyls include, but are not limited to, L-(−)-γ-amino-α-hydroxybutyryl, L(−)-δ-amino-α-hydroxyvaleryl, L-(−)-β-benzyloxycarbonylamino-α-hydroxypropionyl, a L-(−)-δ-benzyloxycarbonylamino-α-hydroxyvaleryl It is noted herein that according to some embodiments of the present invention, other moieties which involve a combination of carbonyl(s), hydroxyl(s) and amino group(s) along a lower alkyl exhibiting any stereochemistry, are contemplated as optional substituents in place of AHB and/or AHP, including, for example, 2-amino-3-hydroxybutanoyl, 3-amino-2-hydroxypentanoyl, 5-amino-3-hydroxyhexanoyl and the likes.

Representative compounds are described in WO 2017/037718.

The Processes:

According to the present embodiments, at least some of the processes described herein are usable for large scale production, preparation or manufacturing of aminoglycoside compounds or intermediates thereof.

Herein, by "large scale" in the context of production of any of the compounds described herein, it is meant a production process in which at least one of the compounds, whether a starting material, an intermediate and/or the final product, is used or produced in an amount of at least one mole, or at least 2 moles, or at least 3 moles, or at least 5 moles, for example, 6, 7, 8, 9, 10, 11, 12, 13, 14, 15, 16, 17, 18, 19, 20, 25, 30, 35, 40, 45, 50 moles, or even more, including any intermediate values therebetween.

A "large scale" process is defined, alternatively or in addition, by the weight of the one or more of the starting materials, the intermediates and/or the final product, such that one or more these materials is/are used or produced in an amount of at least one Kg, or at least 2 Kg, or at least 3 Kg, or at least 5 Kg, for example, 6, 7, 8, 9, 10, 11, 12, 13, 14, 15, 16, 17, 18, 19, 20, 25, 30, 35, 40, 45, 50, 60, 70, 80, 90, 100 Kg, or even more, including any intermediate values therebetween.

A "large scale" process is defined, alternatively or in addition, by the volumes of the reactors used in the process, as comprising at least one production step that is performed in a reactor having a volume of at least 10 liters, or at least 15 liters, or at least 20 liters, or at least 30 liters, or at least 40, 50, 60, 70, 80, 90, 100 liters or even more, including any intermediate values therebetween.

Processes of Preparing Pseudo-Trisaccharide Aminoglycoside Compounds:

According to an aspect of some embodiments of the present invention there is provided a process of preparing a pseudo-trisaccharide aminoglycoside compound represented by Formula I, as described herein. The process, according to some embodiments of the present invention is useful for large scale production, as defined herein, of the aminoglycoside compound.

According to an aspect of some embodiments of the present invention there is provided a process of preparing a pseudo-trisaccharide aminoglycoside compound represented by Formula Ia, as described herein. The process, according to some embodiments of the present invention is useful for large scale production, as defined herein, of the aminoglycoside compound.

According to embodiments of the present invention there is provided a process of preparing a compound represented by Formula I or Ia as described herein, which is usable inter alia for a large scale production of such compounds, which comprises:

preparing a donor compound represented by Formula III as described herein, according to any of the respective embodiments described herein and any combination thereof;

Coupling to the donor compound to a corresponding acceptor, for example, an acceptor as defined herein in any of the respective embodiments (e.g., of Formula II, IIa, IIb or IIc); and De-protecting all the protected groups, to thereby obtain the desired pseudo-trisaccharide aminoglycoside.

According to embodiments of the present invention there is provided a process of preparing a compound represented by Formula I as described herein, which is usable inter alia for a large scale production of such compounds, which comprises:

preparing a donor compound represented by Formula III as described herein, according to any of the respective embodiments described herein and any combination thereof;

coupling the donor compound represented by Formula III with an acceptor compound represented by Formula II:

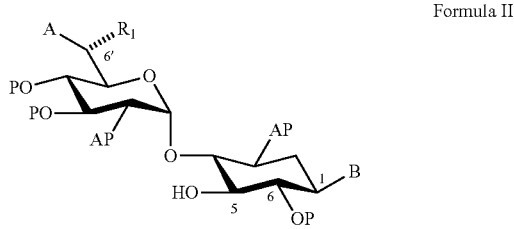

Formula II wherein:

the (rectangular) dashed line represents an S-configuration or an R-configuration at position 6', as described herein;

OP is an acceptor protected hydroxyl group, as described herein;

AP is an acceptor protected amino group, as described herein;

A is an acceptor protected hydroxyl group (OP), as described herein; and

B is an acceptor protected amine group, as described herein, in case $R_4$ is Formula I is hydrogen, and/or a protected or unprotected form of a group defining $R_4$ when $R_4$ is other than hydrogen;

de-protecting the protected hydroxyl groups (the protected acceptor-hydroxy groups and the protected donor-hydroxy groups, when present);

de-protecting the protected amino groups (the protected acceptor-amine groups and the protected donor-amine groups, when present); and optionally, de-protecting any other groups present in a protected form, if present, for example, a protected form of a group defining $R_4$, if present. According to embodiments of the present invention there is provided a process of preparing a compound represented by Formula Ia as described herein, which is usable inter alia for a large scale production of such compounds, which comprises:

preparing a donor compound represented by Formula III as described herein, according to any of the respective embodiments described herein and any combination thereof;

coupling said compound represented by Formula III with a compound represented by Formula IIb:

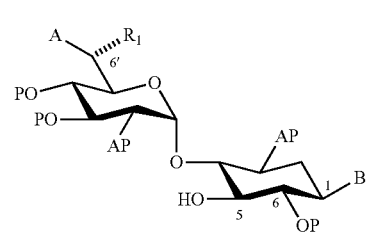

Formula IIb wherein:

the rectangular dashed line represents an S-configuration or an R-configuration at position 6';

OP is an acceptor-protected hydroxyl group;

AP is an acceptor-protected amino group;

A is an acceptor protected hydroxyl group (OP), when $R_2$ in Formula Ia is OR' and R' is hydrogen; an acceptor protected amine group (AP), when $R_2$ is Formula Ia is NR'R" and at least one of R' and R" is hydrogen; or is a protected or unprotected form of a group defining $R_2$ when $R_2$ is other than OH, or other than NHR' or $NH_2$;

B is an acceptor-protected amine group (AP), when $R_4$ is Formula Ia is hydrogen, or a protected or unprotected form of a group defining $R_4$ when $R_4$ is other than hydrogen;

de-protecting said acceptor-protected and donor-protected hydroxyl groups;

de-protecting said acceptor-protected and donor-protected amino groups; and de-protecting said protected form of a group defining $R_2$ and/or said protected from of a group defining $R_4$, if present.

According to some of any of the embodiments described herein, the coupling is effected in the presence of $BF_3$ etherate, although any other coupling agents are contemplated.

According to some of any of the embodiments described herein, the coupling is effected between a compound of Formula II or IIb, as described herein, and a compound of Formula III*:

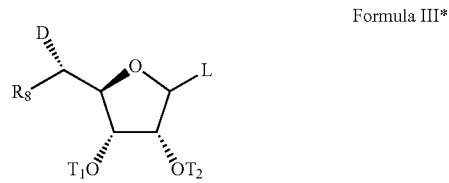

Formula III* wherein D, $R_8$, $OT_1$ and $OT_2$ are as defined herein in any of the respective embodiments, and L is a leaving group, as defined herein.

As used herein, the phrase "leaving group" describes a labile atom, group or chemical moiety that readily undergoes detachment from an organic molecule during a chemical reaction, while the detachment is typically facilitated by the relative stability of the leaving atom, group or moiety thereupon. Typically, any group that is the conjugate base of a strong acid can act as a leaving group. In some embodiments, the leaving group facilitates the coupling reaction between the donor and the acceptor. Representative examples of suitable leaving groups according to some of the present embodiments include, without limitation, imidate (e.g., acetimidate such as trichloroacetimidate), acetate, tosylate, triflate, sulfonate, azide, halide, thiohydroxy, alkoxy, cyanate, thiocyanate, nitro and cyano.

In some embodiments, the inclusion of a leaving group represents an activated form of the compound of Formula III.

In some embodiments, a compound of Formula III is converted to an activated form thereof prior to the coupling.

In some embodiments, the conversion to an activated form is effected in situ, such that a compound of Formula III is converted to its activated form (e.g., Formula III*) in the reaction pot, before or during contacting with a compound of Formula II or IIb and/or with a coupling agent.

In some embodiments, the conversion of a compound of Formula III to an activated form thereof is effected before the coupling is effected, that is, before contacting with a coupling agent and/or an acceptor as described herein.

The acceptor hydroxyl-protected groups and the acceptor amino-protected groups at the various positions of the acceptors of Formula II or IIb can be the same or different at each position.

In some embodiments, for example, in case $R_4$ in Formula I or Ia is other than H, the acceptor of Formula II or IIb is prepared by generating the moiety B, prior to reacting it with the donor.

In some embodiments, B in Formula II or IIb comprises a protected amine group, and further comprises a protected form of a group defining $R_4$ in case $R_4$ is other than hydrogen. For example, when $R_4$ is a group that comprises an amine, the amine is in a form of an amino-protected group, as described herein. When $R_4$ is a group that comprises a guanine or guanidine, the guanine or guanidine is in a protected form. When $R_4$ is a group that comprises hydroxy, the hydroxy is in a form of a hydroxy-protected group, as described herein. Protected forms of groups defining $R_4$ when other than hydrogen are well-known to those skilled in the art and all are encompassed by the present embodiments.

In some embodiments, A in Formula IIb comprises a protected hydroxy group, when $R_2$ is OR' and R' is hydrogen.

In some embodiments, A in Formula IIb comprises a protected amine group, when $R_2$ is NR'R" and one or both of R' and R" is hydrogen. When one or both of R' and R" is other than hydrogen, but comprises an amine, the amine is in a form of an amino-protected group, as described herein. When one or both of R' and R" is a group that comprises hydroxy, the hydroxy is in a form of a hydroxy-protected group, as described herein. Protected forms of groups defining R' and R" when other than hydrogen are well-known to those skilled in the art and all are encompassed by the present embodiments.

The structure of the acceptor compound (of Formula II or IIb) sets the absolute structure of Ring I and Ring II in the resulting compound represented by Formula I or Ia, respectively, according to some embodiments of the present invention.

The structure of the donor compound sets the absolute structure of Ring III in the resulting compound represented by Formula I or Ia according to some embodiments of the present invention, namely the stereo-configuration of the 5" position and the type of $R_8$ in Formula I or Ia.

According to some of any of the embodiments described herein, each of the acceptor hydroxyl-protected group is O-acetyl.

According to some of any of the embodiments described herein, de-protecting the O-acetyl hydroxy-protected groups is effected in a methanolic ammonia solution, as described and exemplified in the Examples section that follows.

According to some of any of the embodiments described herein, each of the acceptor amino-protecting group is a benzyloxycarbonyl (CBz) group.

According to some of any of the embodiments described herein, each of the donor amino-protecting group is a benzyloxycarbonyl (CBz) group.

According to some of any of the embodiments described herein, each of the donor hydroxy-protected groups is a O-benzoyl group.

According to some of any of the embodiments described herein, de-protecting the amino groups is advantageously effected by Pd/C-catalyzed hydrogenation, as described and exemplified in the Examples section that follows.

According to some of any of the embodiments described herein, the compound of Formula I or Ia is a sulfate salt, and the process further comprises converting a compound represented by Formula I or Ia when formed as a free base thereof to the sulfate salt.

According to some of any of the embodiments described herein, the conversion to the sulfate sale is performed by contacting a compound represented by Formula I or Ia in a form of a free base thereof, obtained by coupling the donor and acceptor, with a methanolic solution of $H_2SO_4$, as described and exemplified in the Examples section that follows.

According to some of any of the embodiments described herein, the acceptor compound represented by Formula II or IIb is prepared as described herein in any of the respective embodiments and any combination thereof.

An exemplary process of preparing a compound of Formula I wherein $R_1$ is methyl, a configuration at position 6' is an R-configuration, $R_4$ is hydrogen, and $R_8$ is methyl, is as described herein in the Examples section that follows and is depicted in FIGS. 1-3. In some of any of the embodiments described herein, compound represented by Formula I or Ia, including salts thereof, are prepared by coupling any of the acceptor compounds described herein with a donor compound as described, for example, in WO 2012/066546 and/or WO 2017/037718.

In some of any of the embodiments described herein, compound represented by Formula I or Ia, including salts thereof, are prepared by coupling a donor compound as described herein in any of the respective embodiments, with an acceptor compound as described, for example, in WO 2012/066546 and/or WO 2017/037718.

In some of any of the embodiments described herein, compound represented by Formula I or Ia, including salts thereof, are prepared by coupling any of the acceptor compounds described herein with any of the donor compounds as described herein.

In some of these embodiments, the coupling and/or the protecting groups and their corresponding de-protection and/or the conversion to a sulfate salt, is effected as described herein for any of the respective embodiments and any combination thereof.

Preparation of a Donor Compound:

According to an aspect of some embodiments of the present invention there is provided a process of preparing a donor compound represented by Formula III:

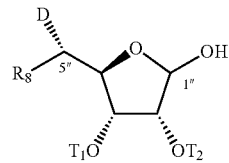

Formula III wherein:

$OT_1$ and $OT_2$ are each independently a donor protected hydroxyl group;

$R_8$ is as defined herein for Formula I or Ia, and is preferably an alkyl, more preferably methyl; and D is a donor protected amino group.

According to some of any of the embodiments described herein, the process as described herein is usable for a large-scale production of a compound of Formula III.

According to some embodiments of the present invention, each of the donor hydroxy-protecting groups is O-benzoyl.

According to some embodiments, the process is effected by:

reacting a compound represented by Formula IIIa:

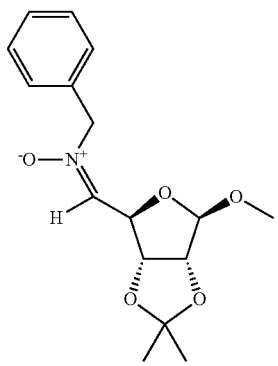

Formula IIIa with a Grignard reagent represented by the Formula $R_8MgX$, wherein X is halide, to thereby obtain stereoselectively a compound represented by Formula IIIb:

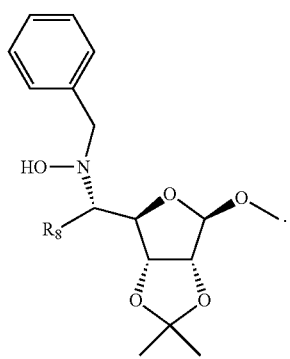

Formula IIIb

By "stereoselectively" it is meant that the depicted stereoisomer is obtained in an optical purity (enantiomeric purity) of at least 60%, or at least 70%, or at least 80%, or at least 90%, or at least 95%, or at least 98%, or at least 99%, or even higher. That means that at least 60%, or at least 70%, or at least 80%, or at least 90%, or at least 95%, or at least 98%, or at least 99%, by moles, of the obtained compound of Formula IIIb has an S-configuration at position respective to 5" in Formula IIIb.

The process continues by converting the compound represented by Formula IIIb to a compound represented by Formula IIIc:

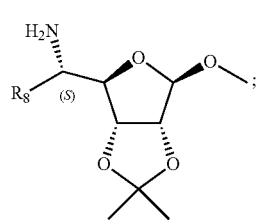

Formula IIIc reacting the compound represented by Formula IIIc with an amino-protecting group to thereby form the D amino-protected group; and reacting the compound represented by Formula IIIc with hydroxy protecting groups to thereby form the $OT_1$ and $OT_2$ hydroxy-protected groups.

The process may further comprise generating a hydroxy group at position 1".

Converting the compound represented by Formula IIIb to a compound represented by Formula IIIc and further reacting the compound represented by Formula IIIc to obtain the donor compound represented by Formula III are performed by maintaining the stereo-configuration at position 5".

By "maintaining stereoconfiguration" it is meant that the optical purity of compounds of Formula IIIc and of Formula III is essentially the same as described herein for compounds of Formula IIIb. By "essentially the same" it is meant that it differs from the optical purity of compounds of Formula IIIb by no more than 10%, preferably by no more than 5%, or no more than 4%, or no more than 3%, or no more than 2%, or no more than 1%, or no more than 0.5%, or no more than 0.1%.

In some embodiments, the optical purity of compounds of Formula IIIc and of Formula III is essentially the same as described herein for compounds of Formula IIIb.

According to some of any of the embodiments described herein, the amino-protecting group is N-benzyloxycarbonyl.

According to some of any of the embodiments described herein, each of the hydroxy-protecting groups is benzoyl.

According to some of any of the embodiments described herein, the process is effected by preparing the compound represented by Formula IIIa by:

converting D-ribose to a dioxolane-protected D-ribose;

oxidizing a hydroxy group at position 5" to a respective aldehyde; and reacting the aldehyde with N-Benzyl hydroxyl amine hydrochloride.

In exemplary embodiments, the compound represented by Formula IIIa is prepared as described in the Examples section that follows for Compound 103.

In exemplary embodiments, D is an N-benzyloxycarbonyl (CBz)-protected amino group, $R_8$ is methyl, and each of $T_1$ and $T_2$ is benzoyl. An exemplary process of preparing such a donor compound, which is also referred to herein as BB-D, is described in detail in the Examples section that follows and is generally depicted in FIG. 1. When L is OH, the donor compound is also referred to herein as BB-D-OH.

In some embodiments, preparing the compound represented by Formula IIIa from D-ribose, reacting the compound represented by Formula IIIa with the Grignard reagent, converting the compound represented by Formula IIIb to the compound represented by Formula IIIc and reacting the compound represented by Formula IIIc with an amino-protecting group to thereby form the D, are performed as a "one pot reaction", namely, by continuously reacting the intermediate product obtained in each of these reaction to thereby provide the following intermediate, and/or without isolating the intermediate compound.

It is to be noted that for any of the embodiments described herein, the methoxy group at position 1" in any of compounds of Formulae IIIa, IIIb and IIIc can be replaced with any other hydroxy-protecting group, as defined herein.

It is to be further noted that for any of the embodiments described herein, the Dioxolane group, protecting the hydroxy groups at positions 2" and 3", can be replaced by any other hydroxy protecting group as defined herein, which can be the same or different from $OT_1$ and $OT_2$ as described herein.

According to some embodiments of the present invention, a process as described herein for preparing a compound of Formula III can be used for preparing a compound of Formula IV:

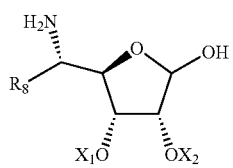

Formula IV wherein:

$R_8$ is as defined herein; and $X_1$ and $X_2$ are each independently hydrogen or a hydroxy protecting group as defined herein.

The process of effected by providing a compound of Formula IIIc, as described herein in any of the respective embodiments; generating respective $OX_1$ and $OX_2$ (in case these are different from the hydroxy-protecting groups in the compound of Formula IIIc), using procedures well known in the art; and generating a hydroxy group at position 1".

In some embodiments, a compound of Formula IV is usable for preparing a compound of Formula III* as described herein, by converting the hydroxy group at position 1" to a respective leaving group, as defined herein.

Processes of Preparing Acceptor Compounds:

According to an aspect of some embodiments of the present invention there is provided a process of preparing an acceptor compound represented by Formula II:

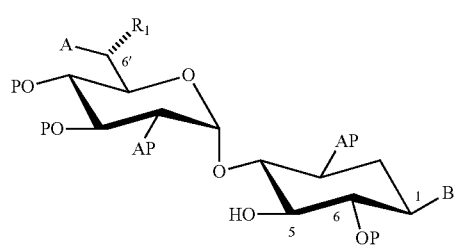

Formula II wherein:

the (rectangular) dashed line represents an S-configuration or an R-configuration at position 6', and is preferably an R-configuration;

$R_1$ is hydrogen, alkyl, cycloalkyl or aryl, and is preferably an alkyl, more preferably methyl;

OP is an acceptor protected hydroxyl group;

AP is an acceptor protected amino group;

A is an acceptor protected hydroxyl group (OP); and

B is an acceptor protected amine group, an acyl, or a protected or unprotected amino-substituted alpha-hydroxy acyl, and is preferably an acceptor protected amino group.

The acceptor hydroxy-protected groups and the acceptor amino-protected groups at the various positions of the acceptors can be the same or different at each position.

The structure of the acceptor compound sets the absolute structure of Ring I and Ring II in the resulting compound of Formula I according to some embodiments of the present invention.

According to some of any of the embodiments described herein, there is provided a process of preparing an acceptor of Formula II as described herein, which is usable for a large scale production of the acceptor or for a large scale production of a compound of Formula I.

According to some of any of the embodiments described herein, there is provided a process of preparing an acceptor of Formula II, which can be used, inter alia, for a large scale production of the acceptor or for a large scale production of a compound of Formula I, which comprises:

providing a compound represented by Formula IIa:

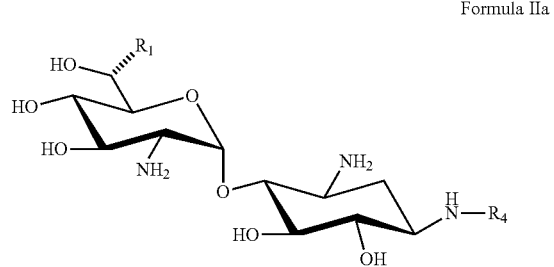

Formula IIa or a pharmaceutically acceptable salt thereof, wherein:

the dashed line denotes a stereoconfiguration at position 6' as described herein, and $R_4$ is hydrogen, acyl or an amino-substituted alpha-hydroxy acyl, preferably hydrogen; converting each of the amino groups to the amino-protected groups; and converting each of the hydroxy groups to the hydroxy-protected groups.

According to some of any of the embodiments described herein, each of the hydroxy-protected groups is O-acetyl.

According to some of any of the embodiments described herein, each of the amino-protected groups is a benzyloxycarbonyl (CBz)-protected amino group.

As discussed herein, such amino-protected groups are substantially less hazardous than the previously described azide groups, and further, advantageously allow performing the de-protection of the amino groups by hydrogenation.

According to some embodiments of the present invention, $R_1$ is methyl, a configuration at position 6' is an R-configuration, and providing the compound of Formula IIa comprises converting G-418 sulfate to the compound represented by Formula IIa.

According to some embodiments of the present invention, this converting comprises converting G-418 to its free base form (e.g., using methodologies known in the art) and contacting G-418 in a form of a free base thereof with a methanolic solution of HCl.

An exemplary process of preparing an exemplary acceptor of Formula II, referred to herein as BB-A, is described in detailed in the Examples section and is depicted in FIG. 2.

In an exemplary process according to the present embodiments, a process as described herein is usable for large scale production of the pseudo-trisaccharide amino glycoside compounds referred to herein as NB124 or ELX-02, and is effected by preparing a donor compound BB-D-OH, as described herein, and an acceptor compound BB-A, as described herein, and coupling BB-D-OH (optionally upon converting it to an activated form such as BB-D) and BB-A to thereby obtain the desired product, possibly as a salt thereof (e.g., a sulfuric acid salt). Such a process is depicted in FIG. 3.

According to an aspect of some embodiments of the present invention there is provided a process of preparing an acceptor compound represented by Formula IIb:

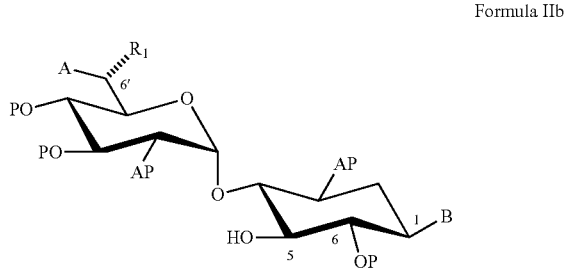

Formula IIb wherein:
the (rectangular) dashed line represents an S-configuration or an R-configuration at position 6', and is preferably an R-configuration;
$R_1$ is hydrogen, alkyl, cycloalkyl or aryl, and is preferably an alkyl, more preferably methyl;
OP is an acceptor protected hydroxyl group;
AP is an acceptor protected amino group;
A and B are as defined herein for Formula IIb.

The acceptor hydroxy-protected groups and the acceptor amino-protected groups at the various positions of the acceptors can be the same or different at each position.

The structure of the acceptor compound of Formula IIb sets the absolute structure of Ring I and Ring II in the resulting compound of Formula Ia according to some embodiments of the present invention.

According to some of any of the embodiments described herein, there is provided a process of preparing an acceptor of Formula IIb as described herein, which is usable for a large scale production of the acceptor or for a large scale production of a compound of Formula Ia.

According to some of any of the embodiments described herein, there is provided a process of preparing an acceptor of Formula IIb, which can be used, inter alia, for a large scale production of the acceptor or for a large scale production of a compound of Formula Ia, which comprises:
providing a compound represented by Formula IIc:

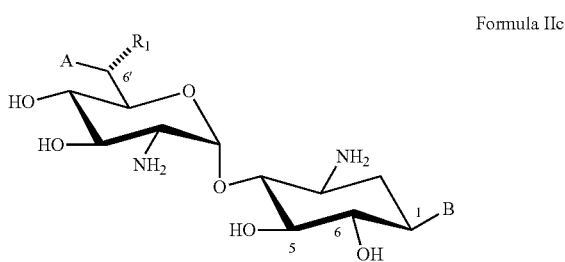

Formula IIc wherein:
the rectangular dashed line represents an S-configuration or an R-configuration at position 6';
A is OH, when $R_2$ in Formula Ia is OR' and R' is hydrogen; NH2 in case $R_2$ is Formula Ia is NR'R" and each of R' and R" is hydrogen; NHR' OR NHR", in case $R_2$ is Formula Ia is NR'R" and one of R' and R" is hydrogen; or is a substituted or unsubstituted alkyl as defined for $R_2$ in Formula Ia;
B is an amine, when $R_4$ is Formula Ia is hydrogen, or an unprotected form of a group defining $R_4$ when $R_4$ is other than hydrogen, as defined herein;
converting each of the amino groups to the amino-protected groups; and converting each of the hydroxy groups to the hydroxy-protected groups.

According to some of any of the embodiments described herein, each of the hydroxy-protected groups is O-acetyl.

According to some of any of the embodiments described herein, each of the amino-protected groups is a benzyloxycarbonyl (CBz)-protected amino group.

Embodiments of the present invention further relate to processes (e.g., large scale processes as defined herein) of preparing intermediate compounds represented by Formula IIIa, IIIb and IIIc, as described herein, and to the compounds represented by Formula IIIa, IIIb and IIIc, as described herein.

Therapeutic Uses:

The compounds presented herein were designed so as to possess a truncation mutation suppression activity, namely the ability to induce readthrough of a premature stop codon mutation. Such an activity renders these compounds suitable for use as therapeutically active agents for the treatment of genetic disorders, and particularly such disorders which are characterized by a truncation mutation.

According to an aspect of some embodiments of the present invention, any of the compounds collectively represented herein by a general Formula I or Ia, and prepared by a process as described herein, are for use in the treatment of a genetic disorder, or for use in the manufacture of a medicament for the treatment of a genetic disorder.

According to an aspect of some embodiments of the present invention there is provided a method of treating a genetic disorder. The method, according to this aspect of the present invention, is effected by administering to a subject in need thereof a therapeutically effective amount of one or more of the compounds presented herein having a general Formula I or Ia, prepared by a process as described herein including any of the respective embodiments of the compounds and any combinations thereof.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "therapeutically effective amount" describes an amount of the polymer being administered which will relieve to some extent one or more of the symptoms of the condition being treated.

The phrase "genetic disorder", as used herein, refers to a chronic disorder which is caused by one or more defective genes that are often inherited from the parents, and which can occur unexpectedly when two healthy carriers of a defective recessive gene reproduce, or when the defective gene is dominant. Genetic disorders can occur in different inheritance patterns which include the autosomal dominant pattern wherein only one mutated copy of the gene is needed for an offspring to be affected, and the autosomal recessive pattern wherein two copies of the gene must be mutated for an offspring to be affected.

The phrase "genetic disorder", as used herein, encompasses a genetic disorder, genetic disease, genetic condition or genetic syndrome.

According to some of any of the embodiments of the present invention, the genetic disorder, genetic disease, genetic condition or genetic syndrome involves a gene having a premature stop codon mutation, or a truncation mutation (nonsense mutation) which leads to improper translation thereof. The improper translation produces a dysfunctional essential protein or causes a reduction or abolishment of synthesis of an essential protein. In the context of the some embodiments of the present invention, the genetic disorders which are contemplated within the scope of the present embodiments are referred to as genetic disorders associated with a premature stop codon mutation and/or a protein truncation phenotype.

According to some of any of the embodiments of the present invention, a genetic disorder associated with a premature stop codon mutation and/or a protein truncation phenotype is treatable by promoting read-through of the complete transcript (mRNA), or in other words, by promoting suppression of the nonsense mutation (the premature stop codon mutation and/or the truncation mutation). The genetic disorder can therefore be a disorder that is treatable by read-through-inducing compounds.

Methods for identification of a genetic disorder associated with a premature stop codon mutation and/or a protein truncation phenotype are well known in the art, and include full or partial genome elucidation, genetic biomarker detection, phenotype classification and hereditary information analysis.

Such methods often result in pairs of mutant/wild type (WT) sequences, and these pairs can be used in known methodologies for identifying if the genetic disorder is associated with a premature stop codon mutation and/or a protein truncation phenotype.

A read-through-inducing activity of compounds for treating such genetic disorders can be established by methods well known in the art.

For example, a plasmid comprising two reporter genes interrupted by a sequence of the mutated gene (the genetic disorder-causing gene) is transected into a protein expression platform, either in full cells or in a cell-free systems, and the ratio between the expression level of the two genes in the presence of a tested compound is measured, typically in series of concentrations and duplications, and compared to the gene expression level ratio of the wild-type and/or to the expression level ratio measured in a control sample not containing the tested compound.

It is noted that the experimental model for read-through activity, namely the nucleotide sequence of gene containing the premature stop codon mutation, is a byproduct of the process of identifying a genetic disorder as associated with a premature stop codon mutation and/or a protein truncation phenotype, and further noted that with the great advances in genomic data acquisition, this process is now well within the skills of the artisans of the art, and that once the mechanism of action of a drug candidate is established, as in the case of genetic disorders which have been shown to be associated with a premature stop codon mutation and/or a protein truncation phenotype, it is well within the skills of the artisans of the art to identify, characterize and assess the efficacy, selectivity and safety of any one of the read-through-inducing compounds presented herein. It is further well within the skills of the artisans of the art to take the read-through-inducing compounds presented herein further though the routine processes of drug development.

Methodologies for testing read-through of a premature stop codon mutation and/or a truncation mutation, referred to herein as read-through activity, are known in the art, and several exemplary experimental methods are provided in the Examples section that follows, by which the read-through-inducing compounds, according to some embodiments of the present invention, can be characterized. It is to be understood that other methods can be used to characterized read-through-inducing compounds, and such methods are also contemplated within the scope of the present invention. Methods such as provided herein can also be adapted for high throughput screening technology that can assay thousands of compounds in a relatively short period of time.

The skilled artisan would appreciate that many in vitro methodologies can be used to characterize read-through-inducing compounds provided herein in terms of safety of use as drugs, and assess the drug candidates in terms of their cytotoxicity versus their efficacy. The skilled artisan would also appreciate that many in vitro methodologies can be used to characterize the read-through-inducing compounds provided herein for eukaryotic versus prokaryotic selectivity, and such methodologies may also be adapted for high throughput screening technology that can assay thousands of compounds in a relatively short period of time.

Exemplary genetic disorders, diseases, conditions and syndromes, which are associated with the presence of at least one premature stop codon or other nonsense mutations include, without limitation, Rett syndrome, cystic fibrosis (CF), Becker muscular dystrophy (BMD), Congenital muscular dystrophy (CMD), Duchenne muscular dystrophy (DMD), Factor VII deficiency, Familial atrial fibrillation, Hailey-Hailey disease, hemophilia A, hemophilia B, Hurler syndrome, Louis-Bar syndrome (ataxia-telangiectasia, AT), McArdle disease, Mucopolysaccharidosis, Nephropathic cystinosis, Polycystic kidney disease, Spinal muscular atrophy (SMA), Tay-Sachs, Usher syndrome, X-linked nephrogenic diabetes insipidus (XNDI) and X-linked retinitis pigmentosa.

In some of any of the embodiments described herein, the genetic disorder is Rett syndrome.

In any of the methods and uses described herein, the compounds described herein can be utilized either per se or form a part of a pharmaceutical composition, which further comprises a pharmaceutically acceptable carrier, as defined herein.

According to an aspect of some embodiments of the present invention, there is provided a pharmaceutical composition which comprises, as an active ingredient, any of the compounds described herein and a pharmaceutically acceptable carrier.

As used herein a "pharmaceutical composition" refers to a preparation of the compounds presented herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the compounds presented herein into preparations which, can be used pharmaceutically. Proper formulation is dependent upon the route of administration chosen.

According to some embodiments, the administration is effected orally. For oral administration, the compounds presented herein can be formulated readily by combining the compounds with pharmaceutically acceptable carriers well known in the art. Such carriers enable the compounds presented herein to be formulated as tablets, pills, dragees, capsules, liquids, gels, syrups, slurries, suspensions, and the like, for oral ingestion by a patient.

Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the compounds presented herein may be dissolved or suspended in suitable liquids, such as fatty oils, liquid paraffin, or liquid polyethylene glycols.

In addition, stabilizers may be added. All formulations for oral administration should be in dosages suitable for the chosen route of administration.

For injection, the compounds presented herein may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active aminoglycoside compounds doses.

For buccal administration, the compositions may take the form of tablets or lozenges formulated in conventional manner.

For administration by inhalation, the compounds presented herein are conveniently delivered in the form of an aerosol spray presentation (which typically includes powdered, liquefied and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compounds presented herein and a suitable powder base such as, but not limited to, lactose or starch.

The compounds presented herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the compounds preparation in water-soluble form. Additionally, suspensions of the compounds presented herein may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds presented herein to allow for the preparation of highly concentrated solutions.

Alternatively, the compounds presented herein may be in powder form for constitution with a suitable vehicle, e.g., sterile, pyrogen-free water, before use.

The compounds presented herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of compounds presented herein effective to prevent, alleviate or ameliorate symptoms of the disorder, or prolong the survival of the subject being treated.

Determination of a therapeutically effective amount is well within the capability of those skilled in the art, especially in light of the detailed disclosure provided herein.

For any compounds presented herein used in the methods of the present embodiments, the therapeutically effective amount or dose can be estimated initially from activity assays in animals. For example, a dose can be formulated in animal models to achieve a circulating concentration range that includes the mutation suppression levels as determined by activity assays (e.g., the concentration of the test compounds which achieves a substantial read-through of the truncation mutation). Such information can be used to more accurately determine useful doses in humans.

Toxicity and therapeutic efficacy of the compounds presented herein can be determined by standard pharmaceutical procedures in experimental animals, e.g., by determining the $EC_{50}$ (the concentration of a compound where 50% of its maximal effect is observed) and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the compounds presented herein which are sufficient to maintain the desired effects, termed the minimal effective concentration (MEC). The MEC will vary for each preparation, but can be estimated from in vitro data; e.g., the concentration of the compounds necessary to achieve 10-90% expression of the whole gene having a truncation mutation, i.e. read-through of the mutation codon. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the chronic condition to be treated, dosing can also be a single periodic administration of a slow release composition described hereinabove, with course of periodic treatment lasting from several days to several weeks or until sufficient amelioration is effected during the periodic treatment or substantial diminution of the disorder state is achieved for the periodic treatment.

The amount of a composition to be administered will, of course, be dependent on the subject being treated, the severity of the affliction, the manner of administration, the judgment of the prescribing physician, etc. Compositions of the present invention may, if desired, be presented in a pack or dispenser device, such as an FDA (the U.S. Food and Drug Administration) approved kit, which may contain one or more unit dosage forms containing the active ingredient. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound according to the present embodiments, formulated in a compatible pharmaceutical carrier may also be prepared, placed in an appropriate container, and labeled for treatment of an indicated condition or diagnosis, as is detailed hereinabove.

Thus, in some embodiments, the pharmaceutical composition is packaged in a packaging material and identified in print, in or on the packaging material, for use in the treatment of a genetic disorder, as defined herein.

In any of the composition, methods and uses described herein, the compounds can be utilized in combination with other agents useful in the treatment of the genetic disorder.

Being primarily directed at treating genetic disorders, which are chronic by definition, the compounds presented herein or pharmaceutical compositions containing the same are expected to be administered throughout the lifetime of the subject being treated. Therefore, the mode of administration of pharmaceutical compositions containing the compounds should be such that will be easy and comfortable for administration, preferably by self-administration, and such that will take the smallest toll on the patient's wellbeing and course of life.

The repetitive and periodic administration of the compounds presented herein or the pharmaceutical compositions containing the same can be effected, for example, on a daily basis, i.e. once a day, more preferably the administration is effected on a weekly basis, i.e. once a week, more preferably the administration is effected on a monthly basis, i.e. once a month, and most preferably the administration is effected once every several months (e.g., every 1.5 months, 2 months, 3 months, 4 months, 5 months, or even 6 months).

As discussed hereinabove, some of the limitations for using presently known aminoglycosides as truncation mutation read-through drugs are associated with the fact that they are primarily antibacterial (used as antibiotic agents). Chronic use of any antibacterial agents is highly unwarranted and even life threatening as it alters intestinal microbial flora which may cause or worsen other medical conditions such as flaring of inflammatory bowel disease, and may cause the emergence of resistance in some pathological strains of microorganisms.

In some embodiments, the compounds presented herein have substantially no antibacterial activity. By "no antibacterial activity" it is meant that the minimal inhibition concentration (MIC) thereof for a particular strain is much higher than the concentration of a compound that is considered an antibiotic with respect to this strain. Further, the MIC of these compounds is notably higher than the concentration required for exerting truncation mutation suppression activity.

Being substantially non-bactericidal, the compounds presented herein do not exert the aforementioned adverse effects and hence can be administered via absorption paths that may contain benign and/or beneficial microorganisms that are not targeted and thus their preservation may even be required. This important characteristic of the compounds presented herein renders these compounds particularly effective drugs against chronic conditions since they can be administered repetitively and during life time, without causing any antibacterial-related adverse, accumulating effects, and can further be administered orally or rectally, i.e. via the GI tract, which is a very helpful and important characteristic for a drug directed at treating chronic disorders.

According to some embodiments, the compounds presented herein are selected and/or designed to be selective towards the eukaryotic cellular translation system versus that of prokaryotic cells, namely the compounds exhibit higher activity in eukaryotic cells, such as those of mammalian (humans) as compared to their activity in prokaryotic cells, such as those of bacteria. Without being bound by any particular theory, it is assumed that the compounds presented herein, which are known to act by binding to the A-site of the 16S ribosomal RNA while the ribosome is involved in translating a gene, have a higher affinity to the eukaryotic ribosomal A-site, or otherwise are selective towards the eukaryotic A-site, versus the prokaryotic ribosomal A-site, as well as the mitochondrial ribosomal A-site which resembles its prokaryotic counterpart.

As used herein the term "about" refers to ±5% or ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Any of the compounds described herein can be or be used in a form of a prodrug, hydrate or solvate thereof.

The term "prodrug" as used herein refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute.

Suitable solvents include, for example, ethanol, acetic acid and the like.

The term "hydrate" refers to a solvate, as defined hereinabove, where the solvent is water.

The terms "hydroxyl" or "hydroxy", as used herein, refer to an —OH group.

As used herein, the term "amine" describes a —NR'R" group where each of R' and R" is independently as described herein, and is, for example, hydrogen, alkyl, cycloalkyl, heteroalicyclic, aryl or heteroaryl, as these terms are defined herein. An amine in which one of R' and R" is other than hydrogen is referred to herein as "modified amine".

As used herein, the term "alkyl" describes an aliphatic hydrocarbon including straight chain and branched chain groups. The alkyl may have 1 to 20 carbon atoms, or 1-10 carbon atoms, and may be branched or unbranched. According to some embodiments of the present invention, the alkyl is a low (or lower) alkyl, having 1 to 6, or 1 to 4, carbon atoms (namely, methyl, ethyl, propyl and butyl).

Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. In some embodiments, the alkyl is a lower alkyl, including 1-6 or 1-4 carbon atoms.

An alkyl can be substituted or unsubstituted. When substituted, the substituent can be, for example, one or more of an alkyl (forming a branched alkyl), an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow. An alkyl substituted by aryl is also referred to herein as "alkaryl", an example of which is benzyl.

Whenever "alkyl" is described, it can be replaced also by alkenyl or alkynyl. The term "alkyl" as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond, e.g., allyl, vinyl, 3-butenyl, 2-butenyl, 2-hexenyl and i-propenyl. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" refers to an all-carbon monocyclic or fused ring (i.e., rings which share an adjacent pair of carbon atoms), branched or unbranched group containing 3 or more carbon atoms where one or more of the rings does not have a completely conjugated pi-electron system, and may further be substituted or unsubstituted. Exemplary cycloalkyl groups include, for example, cyclopropyl, cyclobutyl, cyclopentyl, cyclohexyl, or cyclododecyl. The cycloalkyl can be substituted or unsubstituted. When substituted, the substituent can be, for example, one or more of an alkyl, an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow.

The term "aryl" describes an all-carbon monocyclic or fused-ring polycyclic (i.e., rings which share adjacent pairs of carbon atoms) groups having a completely conjugated pi-electron system. The aryl group may be unsubstituted or substituted by one or more substituents. When substituted, the substituent can be, for example, one or more of an alkyl, an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. Representative examples are thiadiazole, pyridine, pyrrole, oxazole, indole, purine and the like. The heteroaryl group may be unsubstituted or substituted by one or more substituents. When substituted, the substituent can be, for example, one or more of an alkyl, an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow.

The term "heteroalicyclic", as used herein, describes a monocyclic or fused ring group having in the ring(s) one or more atoms such as nitrogen, oxygen and sulfur. The rings may also have one or more double bonds. However, the rings do not have a completely conjugated pi-electron system. Representative examples are morpholine, piperidine, piperazine, tetrahydrofurane, tetrahydropyrane and the like. The heteroalicyclic may be substituted or unsubstituted. When substituted, the substituent can be, for example, one or more of an alkyl, an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow.

The term "halide", as used herein, refers to the anion of a halo atom, i.e. $F^-$, $Cl^-$, $Br^-$ and $I^-$.

The term "halo" refers to F, Cl, Br and I atoms as substituents.

The term "alkoxide" refers to an Ra—O$^-$ anion, wherein Ra is alkyl, cycloalkyl, aryl, heteroaryl or heteroalicyclic.

The term "alkoxy" refers to an ORa group, wherein Ra is as defined herein, but other than hydrogen.

The term "hydroxyalkyl," as used herein, refers to an alkyl group, as defined herein, substituted with one or more hydroxy group(s), e.g., hydroxymethyl, 2-hydroxyethyl and 4-hydroxypentyl.

The term "aminoalkyl," as used herein, refers to an alkyl group, as defined herein, substituted with one or more amino group(s).

The term "alkoxyalkyl," as used herein, refers to an alkyl group substituted with one alkoxy group, e.g., methoxymethyl, 2-methoxyethyl, 4-ethoxybutyl, n-propoxyethyl and t-butylethyl.

The term "trihaloalkyl" refers to —CX$_3$, wherein X is halo, as defined herein. An exemplary haloalkyl is CF$_3$.

A "guanidino" or "guanidine" or "guanidinyl" group refers to an —RaNC(=NRd)-NRbRc group, where each of Ra, Rb, Rc and Rd can be as defined herein for R' and R".

A "guanyl" or "guanine" group refers to an RaRbNC(=NRd)- group, where Ra, Rb and Rd are as defined herein.

In some of any of the embodiments described herein, the guanidine group is —NH—C(=NH)—NH$_2$.

In some of any of the embodiments described herein, the guanyl group is H$_2$N—C(=NH)— group.

Any one of the amine (including modified amine), guanidine and guanine groups described herein is presented as a free base form thereof, but is meant to encompass an ionized form thereof at physiological pH, and/or within a salt thereof, e.g., a pharmaceutically acceptable salt thereof, as described herein.

For any one of the alkyl, cycloalkyl, aryl, alkaryl, heteroaryl, heteroalicyclic, and acyl described herein, alternative substituents include, but are not limited to, sulfonate, sulfoxide, thiosulfate, sulfate, sulfite, thiosulfite, phosphonate, thiohydroxy, thioalkoxy, thioaryloxy, cyano, nitro, azo, sulfonamide, carbonyl, thiocarbonyl, C-carboxylate, O-carboxylate, N-thiocarbamate, O-thiocarbamate, oxo, thiooxo, oxime, acyl, acyl halide, azo, azide, urea, thiourea, N-carbamate, O-carbamate, C-amide, N-amide, hydrazine and hydrazide, as these terms are defined herein.

The term "cyano" describes a —C≡N group.

The term "nitro" describes an —NO$_2$ group.

The term "sulfate" describes a —O—S(=O)$_2$—ORa end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—ORa end group or a —O—S(=S)(=O)—O— linking group, as these phrases are defined hereinabove, where Ra is as defined hereinabove.

The term "sulfite" describes an —O—S(=O)—O—Ra end group or a —O—S(=O)—O— group linking group, as these phrases are defined hereinabove, where R' is as defined hereinabove.

The term "thiosulfite" describes a —O—S(=S)—O—Ra end group or an —O—S(=S)—O— group linking group, as these phrases are defined hereinabove, where Ra is as defined hereinabove.

The term "sulfinate" describes a —S(=O)—ORa end group or an —S(=O)—O— group linking group, as these phrases are defined hereinabove, where Ra is as defined hereinabove.

The term "sulfoxide" or "sulfinyl" describes a —S(=O)Ra end group or an —S(=O)— linking group, as these phrases are defined hereinabove, where Ra is as defined hereinabove.

The term "sulfonate" describes a —S(=O)$_2$—Ra end group or an —S(=O)$_2$— linking group, as these phrases are defined hereinabove, where R' is as defined herein.

The term "S-sulfonamide" describes a —S(=O)$_2$—NRaRb end group or a —S(=O)$_2$—NR'— linking group, as these phrases are defined hereinabove, with Ra being as defined herein and Rb is as defined herein for Ra, independently.

The term "N-sulfonamide" describes an RaS(=O)$_2$—NRb- end group or a —S(=O)$_2$—NRa- linking group, as these phrases are defined hereinabove, where Ra and Rb are as defined herein.

The term "carbonyl" or "carbonate" as used herein, describes a —C(=O)—Ra end group or a —C(=O)— linking group, as these phrases are defined hereinabove, with Ra as defined herein.

The term "thiocarbonyl" as used herein, describes a —C(=S)—Ra end group or a —C(=S)— linking group, as these phrases are defined hereinabove, with Ra as defined herein.

The term "oxo" as used herein, describes a (=O) group, wherein an oxygen atom is linked by a double bond to the atom (e.g., carbon atom) at the indicated position.

The term "thiooxo" as used herein, describes a (=S) group, wherein a sulfur atom is linked by a double bond to the atom (e.g., carbon atom) at the indicated position.

The term "oxime" describes a =N—OH end group or a =N—O— linking group, as these phrases are defined hereinabove.

The term "acyl halide" describes a —(C=O)Rd group wherein Rd is halide, as defined hereinabove.

The term "azo" or "diazo" describes an —N=NRa end group or an —N=N— linking group, as these phrases are defined hereinabove, with Ra as defined hereinabove.

The term "azide" describes an —N$_3$ end group.

The term "carboxylate" as used herein encompasses C-carboxylate and O-carboxylate.

The term "C-carboxylate" describes a —C(=O)—ORa end group or a —C(=O)—O— linking group, as these phrases are defined hereinabove, where Ra is as defined herein.

The term "O-carboxylate" describes a —OC(=O)Ra end group or a —OC(=O)— linking group, as these phrases are defined hereinabove, where Ra is as defined herein.

A carboxylate can be linear or cyclic. When cyclic, Ra and the carbon atom are linked together to form a ring, in C-carboxylate, and this group is also referred to as lactone. Alternatively, Ra and O are linked together to form a ring in O-carboxylate. Cyclic carboxylates can function as a linking group, for example, when an atom in the formed ring is linked to another group.

The term "thiocarboxylate" as used herein encompasses C-thiocarboxylate and 0-thiocarboxylate.

The term "C-thiocarboxylate" describes a —C(=S)—ORa end group or a —C(=S)—O— linking group, as these phrases are defined hereinabove, where Ra is as defined herein.

The term "O-thiocarboxylate" describes a —OC(=S)Ra end group or a —OC(=S)— linking group, as these phrases are defined hereinabove, where Ra is as defined herein.

A thiocarboxylate can be linear or cyclic. When cyclic, Ra and the carbon atom are linked together to form a ring, in C-thiocarboxylate, and this group is also referred to as thiolactone. Alternatively, Ra and O are linked together to form a ring in O-thiocarboxylate.

Cyclic thiocarboxylates can function as a linking group, for example, when an atom in the formed ring is linked to another group.

The term "carbamate" as used herein encompasses N-carbamate and O-carbamate.

The term "N-carbamate" describes an RbOC(=O)—NRa- end group or a —OC(=O)—NRa- linking group, as these phrases are defined hereinabove, with Ra and Rb as defined herein.

The term "O-carbamate" describes an —OC(=O)—NRaRb end group or an —OC(=O)—NRa- linking group, as these phrases are defined hereinabove, with Ra and Rb as defined herein.

A carbamate can be linear or cyclic. When cyclic, Ra and the carbon atom are linked together to form a ring, in O-carbamate. Alternatively, Ra and O are linked together to form a ring in N-carbamate. Cyclic carbamates can function as a linking group, for example, when an atom in the formed ring is linked to another group.

The term "carbamate" as used herein encompasses N-carbamate and O-carbamate.

The term "thiocarbamate" as used herein encompasses N-thiocarbamate and O-thiocarbamate.

The term "O-thiocarbamate" describes a —OC(=S)—NRaRb end group or a —OC(=S)—NRa- linking group, as these phrases are defined hereinabove, with Ra and Rb as defined herein.

The term "N-thiocarbamate" describes an RbOC(=S)NRa- end group or a —OC(=S)NRa- linking group, as these phrases are defined hereinabove, with Ra and Rb as defined herein.

Thiocarbamates can be linear or cyclic, as described herein for carbamates.

The term "dithiocarbamate" as used herein encompasses S-dithiocarbamate and N-dithiocarbamate.

The term "S-dithiocarbamate" describes a —SC(=S)—NRaRb end group or a —SC(=S)NR'— linking group, as these phrases are defined hereinabove, with Ra and Rb as defined herein.

The term "N-dithiocarbamate" describes an RbSC(=S)NRa- end group or a —SC(=S)NRa- linking group, as these phrases are defined hereinabove, with Ra and Rb as defined herein.

The term "urea", which is also referred to herein as "ureido", describes a —NRaC(=O)—NRbRc end group or a —NRaC(=O)—NRb- linking group, as these phrases are defined hereinabove, where Ra and Rb are as defined herein and Rc is as defined herein for Ra and Rb, independently.

The term "thiourea", which is also referred to herein as "thioureido", describes a —NRa-C(=S)—NRbRc end group or a —NRa-C(=S)—NRb- linking group, with Ra, Rb and Rc as defined herein.

The term "amide" as used herein encompasses C-amide and N-amide.

The term "C-amide" describes a —C(=O)—NRaRb end group or a —C(=O)—NRa- linking group, as these phrases are defined hereinabove, where Ra and Rb are as defined herein.

The term "N-amide" describes a RaC(=O)—NRb- end group or a RaC(=O)—N- linking group, as these phrases are defined hereinabove, where Ra and Rb are as defined herein.

The term "hydrazine" describes a —NRa-NRbRc end group or a —NRa-NRb- linking group, as these phrases are defined hereinabove, with Ra, Rb, and Rc as defined herein.

As used herein, the term "hydrazide" describes a —C(=O)—NRa-NRbRc end group or a —C(=O)—NRa- NRb- linking group, as these phrases are defined hereinabove, where Ra, Rb and Rc are as defined herein.

As used herein, the term "thiohydrazide" describes a —C(=S)—NRa-NRbRc end group or a —C(=S)—NRa-NRb- linking group, as these phrases are defined hereinabove, where Ra, Rb and Rc are as defined herein.

As used herein, the term "imidate" described a —O—C(=NRa)-Rb- end group or —O—C(=NRa)- linking group, with Ra and Rb as defined herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Preparation of BB-D-OH

The general synthetic pathway for the large scale production of BB-D-OH is depicted in FIG. 1.

Generally, hereinbelow, an "equivalent" is referred to as a weight unit.

The term "vol.", "vol", or "Vol." refers to a volume ratio to one volume equivalent (v/v). For example, when 10 Vol. is used with 1 equivalent, it is meant that for one gram of a compound, an indicated volume of a solvent or any other reagent is 10-times the volume of one gram of that compound.

The term "w/w" or "% w/w" describes weight percent of the indicated compound of the total weight of the reaction mixture of reagent it is added to.

The term "v/w" describes a volume to weight ratio, in ml/grams units.

The phrase "concentrated up to a v/w" or "concentrated up to a v/v" describes removal of a solvent until the indicated v/w or v/v of the solvent and reagent/product/intermediate is achieved.

Preparation of Compound 107 (FIG. 1, Stage 1a-g)
Preparation of Intermediate Compound 101 (FIG. 1, Stage 1a):

A mixture of methanol (10 vol.) and D-Ribose (1 mol equivalent) was stirred at 25(±5) ° C. for 5-10 minutes. Acetone (12 vol.) was then added and the reaction mixture was stirred at 25(±)5° C. for 5-10 minutes. Con. HCl (0.1 vol.), was thereafter added and the reaction mixture was stirred for 5-10 minutes at a temperature below 30° C. The temperature was then raised to 55(±)5° C. (reflux) and maintained for 2 hours. The reaction was monitored by TLC. Once the reaction was completed, the reaction mixture was cooled to 15(±)5° C., and a saturated sodium bicarbonate solution (2.5 vol.), at a temperature below 30° C., was added and the mixture was stirred at 25(±)5° C. for 30 minutes. Thereafter, the reaction mixture was concentrated up to 3-4 v/w under vacuum at a temperature below 50° C., cooled to 25(±)5° C., diluted with water (10 vol.) and dichloromethane (DCM; 10 vol.) and stirred for 10-15 minutes at 25(±5°) C. The phases were separated and the aqueous layer was extracted with DCM (5 vol.). The combined organic layers (DCM) were washed with water (2×5 Vol.) and brine solution (5 vol.), dried over anhydrous sodium sulfate (1 w/w; 1% weight), filtered, and the filtrate was concentrated to minimal volume under reduced pressure at a temperature below 40° C. A sample of the resulting intermediate was de-gassed under vacuum at a temperature below 40° C. for 1 hour and sent to quality check QC for GC purity. The concentrated solution, containing the intermediate Compound 101 was co-distilled with acetonitrile (2 vol.) under vacuum at a temperature below 45° C., the obtained reaction mixture was cooled to 25(±)5° C. and acetonitrile (1.5 vol.) was added at a temperature below 25(±5°) C. The obtained mixture was unloaded into a cleaned container at 25(±5°) C. The reactor was washed with acetonitrile (0.5 vol.) and unloaded into the above container.

Preparation of Compound 102 (FIG. 1, Stage 1b):

Acetonitrile (8 vol.) and Dess-Martin periodinane (DMP) (1.3 mol equivalents) were added under nitrogen atmosphere at 25(±)5° C. into the reactor, the mixture was cooled to 5(±)5° C. and stirred for 10-15 minutes and Compound 101 (Stage-1a compound), dissolved in acetonitrile, was added slowly to the reaction mixture at 5(±)5° C. for 2-3 hours. The temperature thereafter was raised to 15(±)3° C. and the reaction mixture was stirred for additional 2 hours. The reaction was monitored by GC. Once the reaction was completed, ethyl acetate (10 Vol.) was added at 15(±)3° C., the obtained reaction mixture was cooled to 5(±)5° C. and a solution of sodium thiosulfate dissolved in saturated bicarbonate solution was added. The reaction mixture was stirred at 25(±)5° C. for 1 hour, sodium chloride (4 w/w; 4% weight) was added, and the obtained mixture was stirred at 25(±)5° C. for 15-20 minutes, and then filtered. Thereafter, the layers were separated, the aqueous layer was extracted with ethyl acetate (5 vol), and the combined organic layers were washed with saturated bicarbonate solution followed by brine solution and dried over sodium sulphate (1 w/w; 1 wt. %). The mixture was filtered and the filtrate was concentrated to minimal volume under reduced pressure at a temperature below 40° C. The obtained residue was co-distilled with DCM (2 vol.) under vacuum, several (2-3) times at a temperature below 40° C. DCM (10 v/w) was thereafter at a temperature of 25(±)5° C. and the mixture was stirred for 5 minutes. A sample of the obtained mixture was sent to QC for GC analysis.

Preparation of Compound 103 (FIG. 1, Stage 1c):

Magnesium sulphate (0.5% w/w) was added to the reaction mixture obtained in stage 1b) at 25(±5) ° C. and the obtained mixture was stirred for 5 minutes. N-Benzyl hydroxyl amine hydrochloride (0.65 mol equivalents) was then added and the reaction mixture was stirred for 5-10 minutes at 25(±)5° C., thereafter cooled to 10(±)5° C. and sodium carbonate (0.25 mol equivalents×4) was added slowly and portion-wise at the same temperature with intervals of 5-10 minutes. The temperature was raised to 25(±)5° C. and the mixture was stirred for 2 hours. A sample of the obtained mixture was sent to QC for GC analysis. The reaction mixture was filtered and the resulting wet cake was slurry washed with DCM (1.5 v/w). After filtration, the combined filtrates were washed with water (5 v/w) followed by brine solution. The organic layer was dried over sodium sulphate (1% w/w), filtered and concentrated under reduced pressure to minimal volume at a temperature below 40° C. THF (2 Vol.) was added to the obtained residue and the mixture was co-distilled under vacuum at a temperature below 45° C. THF (10 v/w) was thereafter added and a sample of the obtained product was sent to QC for MC & HPLC purity.

Preparation of Compound 104 (FIG. 1, Stage 1d):

The reaction mixture obtained in stage 1c was cooled to −70(±)5° C., and a solution of Methyl Magnesium chloride in THF (2.5 v/w) was added thereto at −70(±)5° C. over a period of 2-3 hours. The reaction mixture was stirred at −70(±)5° C. for 2 hours, and then a 0(±)5° C. for 1 hour. A sample was sent to QC for HPLC analysis. The reaction mixture was poured into ammonium chloride solution slowly under nitrogen atm. at 0(±)10° C., ethyl acetate (10 v/w) was added to and the obtained mixture was stirred for 10 minutes at 25(±5°) C. The phases were thereafter separated and the aqueous layer was extracted with ethyl acetate (5 v/w). The combined organic layers were washed with water (5 v/w) and a brine solution, dried over anhydrous sodium sulphate (1% w/w), filtered and concentrated under vacuum up to 1-2 volumes (v/v) at a temperature below 40° C. The reaction mixture was then cooled to 25(±)5° C., methanol (5 v/w) was added at 25(±5°) C, and the obtained mixture was co-distilled under vacuum up to 2-3 volumes (v/v) at a temperature below 40° C. The reaction mixture was cooled to 25(±)5° C., stirred at 25(±)5° C. for 1 hour, and then at −40(±)5° C. for 2 hours. The obtained solids were filtered off, washed with chilled methanol (−30(±)5° C.) (1 v/w) and dried under vacuum at 35(±)5° C. for 6 hours. A sample of the obtained product was sent to QC for LOD.

Preparation of Compound 105 (FIG. 1, Stage 1e):

Methanol (10 vol.) was added to Compound 104 obtained in stage 1d (1 mol equivalent) and the mixture was stirred at 25(±)5° C. for 5-10 minutes. Para-toluene sulfonic acid (PTSA) (1.4 mol equivalents) was added and the mixture was stirred at 25(±)5° C. for 5-10 minutes. The temperature was then raised to 64(±)3° C. (reflux) and maintained for 2 hours. A sample was sent to QC for HPLC monitoring. The reaction mixture was concentrated until 3-4 v/w under vacuum at a temperature below 45(±)3° C. and was thereafter cooled to 25(±)5° C., diluted with water (10 v/w) at 25(±)5° C., and stirred for 10-15 minutes. The reaction mixture was then added to a saturated sodium bicarbonate solution slowly at a temperature below 25(±)5° C., stirred for 30-60 minutes, and extracted with ethylacetate. The combined organic phase was dried over sodium sulphate (1% w/w), filtered and concentrated to minimal volume under reduced pressure at a temperature below 40(±5°) C. The obtained product was co-distilled with methanol (3 vol.) at a temperature below 45(±)5° C. and cooled to 25(±5°) C. Methanol (3 vol.) was added a sample of the obtained mixture was sent to QC for HPLC purity.

Preparation of Compound 106 (FIG. 1, Stage 1f):

A mixture of Compound 105 obtained in Stage 1e was put in an autoclave, the reaction mixture was diluted with methanol (8 vol.) at 25(±)5° C., and the obtained mixture was degassed with nitrogen for 5-10 minutes. 10% Palladium carbon (50% wet, 0.1% w/w) was added and the reaction mixture was flushed with nitrogen twice (each time with 3 kg of $H_2$) at 25(±5°) C. 4-5 kg of hydrogen pressure was then applied and the reaction mixture was heated to 50(±)5° C. for 4-5 hours. The reaction was monitored by TLC. Once the reaction was completed, the reaction mixture was cooled to 25(±)5° C., filtered through celite bed under nitrogen atmosphere and the celite bed was washed with methanol. The combined filtrates were filtered through 0.5 mincron filter and distilled under vacuum up to 10 volumes remains. A sample of the obtained product was sent to QC for GC purity.

Preparation of Compound 107 (FIG. 1, Stage 1g):

The mixture containing Compound 106 obtained in stage if was cooled to 10(±)5° C. and sodium carbonate (3.0 mol equivalents) was added. The reaction mixture was stirred for 15-20 minutes and a 50% CBz Chloride in toluene solution (1.0 mol equivalents) was added thereto while maintaining a temperature of 10(±)5° C. for 2 hours. The reaction was monitored by TLC. Once the reaction was completed, the reaction mixture was filtered and washed with methanol (3 vol.) at 25(±5°) C. The solvent was distilled off under vacuum up to 1-2 volumes remains at a temperature below 40(±)5° C. and the resulting mixture was cooled to 25(±)5° C. and diluted with ethyl acetate (3 Vol.). The phases were separated and the organic phase was washed with saturated sodium bicarbonate solution (1.5 vol.) and water (1 vol.), dried over sodium sulfate (1% w/w) and filtered.

The organic solvent was distilled completely under vacuum at a temperature below 40(±)5° C., to thereby obtain isolated Compound 107.

Scale up batch was completed on 60 Kg scale, yielding, after isolation, 33.9 Kg (27% overall yield) of the S-isomer Compound 107 (99.5% optical purity).

Preparation of Compound 108 (FIG. 1, Stage 2):

For the preparation of Compound 108, after filtration of sodium sulfate, the solution containing Compound 107 was distilled to minimal volume, the residue was diluted with acetonitrile (2 vol.), and the obtained mixture was co-distilled in vacuum at 40(±5°) C. The mixture was thereafter cooled to 25(±)5° C., acetonitrile (2 vol.) was added and the mixture was transferred to the next step.

Acetonitrile (8 vol.) was added, followed by triethylamine (3.2 mol equivalents) and 4-N,N-Dimethylaminopyridine (DMAP, 0.1 mol equivalents) at 25(±)5° C., the reaction mixture was cooled to 5(±)5° C. and benzoyl chloride (59 mL; 1.2 mol equivalent) was added. The reaction mixture was stirred at 5(±)5° C. for 2 hours. A sample was sent to QC for HPLC monitoring. Once the reaction was completed, saturated sodium bicarbonate solution (3 vol.) was added at 25(±)5° C. and the obtained mixture was stirred for 1-2 hours. Then the mixture was extracted with ethyl acetate (5 vol.), the phases were separated and the organic phase was dried over $Na_2SO_4$, filtered and the solvent was evaporated completely under vacuum at a temperature below 40(±)5° C. to afford Compound 108 as a viscous liquid.

Scale up batch was completed on 30 Kg scale, yielding, after isolation, 37.14 Kg (75%) of Compound 108.

Preparation of BB-D-OH:

For the preparation of BB-D-OH, after filtration of sodium sulfate, the solution containing Compound 108 was distilled to minimal volume and acetic acid was added. The solvents were co-evaporated. Acetic acid was added to the obtained residue and the mixture was transferred to the next step.

30% Sulfuric acid solution (3 vol.) was added slowly at 25(±)5° C. over a period of 1-2 hours, and the reaction mixture was then heated to 28(±)5° C. and stirred 36 hours at this temperature. A sample was sent to QC for SM content by HPLC. Once the reaction was completed, the reaction mixture was cooled to 25(±)5° C., diluted with dichloromethane (10 vol.) and stirred for 30 minutes. The reaction mixture was thereafter allowed to settle for 1 hour and bottom organic and upper aqueous layers were separated. The DCM layer was washed with water (5 vol.×3), saturated sodium bicarbonate solution and brine, dried over sodium sulfate and filtered. The filtrate was concentrated under vacuum at a temperature below 30(±)5° C. to thereby obtain the crude product as thick syrup.

Purification of BB-D-OH:

The obtained crude product was dissolved in dichloromethane, absorbed on silica gel (100-200 mesh), (3% w/w) at 25(±)5° C. and dried.

Dichloromethane (20 vol.) was added to the Silica gel (100-200 mesh; 12 v/w; 1.2 kg) at 25(±)5° C. and the mixture was poured into a column at 25(±5°) C. The column was run with 10 vol. of dichloromethane at 25(±)5° C. for proper bed formation. Silica-absorbed Stage-3 crude product was packed on the top of the column, and preliminary elution using dichloromethane (10 vol.), followed by 1% ethyl acetate in dichloromethane (20 vol.) was performed to elute non-polar impurities. 2.5% Ethyl acetate in dichloromethane (150 vol.) was then used as eluent to recover residues of Compound 108. After complete elution of Compound 108, the column was eluted with 15% Ethyl acetate in dichloromethane until all the BB-D-OH product was eluted. Pure fractions were collected and samples were sent to QC for purity. All accepted fractions were combined and concentrated at a temperature below 30(±)5° C. to minimal volume and stored as a DCM solution. The sample was submitted to QC for complete analysis.

One scale up batch was completed on 37.1 Kg scale, affording, after column purification, 20.6 Kg of BB-D (57% yield) with 92% purity (as determined by HPLC).

Another scale up batch was completed on 38.7 Kg scale, affording, after column purification, 19.8 Kg (53% yield) with 95% purity (as determined by HPLC).

Example 2

Preparation of BB-A

The general synthetic pathway for the large scale production of BB-A is depicted in FIG. 2.

G418 sulfate salt is converted to a free base form of G418 (Compound 111) using methods known in the art.

Preparation of 6-Methyl Paromamine (Compound 112, FIG. 2, Stage-2):

A mixture of purified G-418 (as a free base; 1.0 mol equivalent), and a methanolic solution of HCl (MeOH HCl; 10 vol) was heated to 70(±5) ° C. for 24 hours. Reaction progress was monitored by HPLC, and indicated that after 24 hours, G-418 was about 4%. The methanol (⅔ of volume) was then distilled off under vacuum at 70(±5) ° C. The reaction mixture was cooled to 30(±5) ° C. and MeOH HCl (10 vol) was added thereto. The obtained mixture was heated to 70(±5) ° C. for 24 hours. Reaction progress was monitored by HPLC, and indicated that after 48 hours, G-418 was about 0.5%. The reaction mixture then was cooled to 5-10° C. and stirred for 1-2 hours, then filtered and dried on the filter for 20-30 minutes. The obtained solids were transferred to a reactor containing ethanol. The mixture was cooled to 0-10° C. and stirred for 1-2 hours at 5-10° C., then filtered, washed with cold ethanol and dried under vacuum for 5-6 hours at 50(±5) ° C.

Acid cleavage of G-418 scale up reaction was completed on 16.4 Kg scale, yielding, after isolation, 12.7 Kg (85%) of 6-methylparomamine, containing 0.47% of G418.

Preparation of Compound 113 (CBz-Protection of 6-Methylparomamine, FIG. 2, Stage-3):

6-Methylparomamine (Compound 112, 1 mol equivalent) and DIPEA (10 mol equivalents) were dissolved in acetone (15 vol) and water (15 vol). CBzCl (4 mol equivalents) (as a 50% solution in Toluene) was added at 30(±5) ° C. and the reaction mixture was stirred for 24 hours. Thereafter, the mixture was diluted with water (10 vol), stirred for 15-20 minutes and then filtered. The obtained solid was stirred in acetone (20 vol) at 30(±5) ° C. for 1-2 hours, filtered under vacuum and the obtained slurry was washed with Acetone (5 vol). The obtained product was dried under vacuum for 3-4 hours at 50-60° C. to afford a crude Compound 113 as a white solid.

CBz protection reaction was completed on 12.5 kg scale, yielding, after isolation, 15.8 Kg of tris-CBz-6-methylparomamine (82% yield; 93% purity as determined by HPLC).

Preparation of BB-A (Acetyl Protection of Tris-CBz-6-Methylparomamine; FIG. 2):

Tris-CBz-6-methylparomamine (Compound 113, 1.0 mol equivalent) was dissolved in pyridine (2 vol) and DMF (3 vol), DMAP (0.1 mol equivalent) was added and the obtained reaction mixture was stirred for 10-15 minutes at 30(±5) ° C. Acetic anhydride was slowly added lot-wise (1+1+1+1+0.5 mol equivalent) to the reaction mixture at 30(±5) ° C. Reaction progress was monitored by HPLC. Once the reaction was completed, the reaction mixture was diluted with water (10 vol) and ethyl acetate (10 vol) and stirred for 10-15 minutes. The organic layer was thereafter separated and the aqueous layer was extracted with ethyl acetate (5 vol). The combined organic layer was washed with 20% aqueous HCl solution (10 vol), water (10 vol) and brine solution (10 vol), dried over $Na_2SO_4$ and concentrated under reduced pressure to afford the crude product.

The crude product was purified on a Silica gel (100-200) mesh (20 w/w) column using ethyl acetate and DCM (15-40%), as eluent. Three main fractions containing the product were collected and concentrated under vacuum.

Scale up reaction was completed on 15.5 Kg scale, yielding, after isolation, 16.5 Kg (86%) of BB-A.

Example 3

Preparation of ELX-02

The general synthetic pathway for the large scale production of ELX-02 is depicted in FIG. 3.

Preparation of BB-D (In Situ):

To a solution of Compound BB-D-OH (FIG. 1) in DCM (1.5 mol equivalent), DCM (8 vol.) was added at 25(±)5° C. and the mixture was stirred for 10-20 minutes. The solution was thereafter cooled −5(±)5° C., trichloroacetonitrile (3 mol equivalents) was added thereto at −5(±5) ° C. and the obtained mixture was stirred for 5-10 minutes. DBU (0.15 mol equivalent) solution in DCM (0.5 vol.) was added slowly to the reaction mixture, while maintaining the temperature at −5(±5) ° C. and the mixture was stirred for 2 hours. Reaction progress was monitored by HPLC. Once the reaction was completed, 20% ammonium chloride solution (10 vol.) was added slowly to the reaction mixture at 10(±5°) C. The layers were separated, the organic layer was washed with 20% sodium chloride solution (10 vol.) at 5(±)5° C. and dried over anhydrous sodium sulfate (1% w/w).

Preparation of Compound 121 (Coupling of BB-A and BB-D, FIG. 3):

The organic layer containing in-situ prepared BB-D and BB-A (1 mol equivalent) were mixed together at 10(±)5° C.

and stirred for 10-15 minutes. Molecular sieves (0.5% w/w) were added and the mixture was stirred for 10-15 minutes and thereafter cooled to −15(±5°) C. BF$_3$-Etherate (0.1 mol equivalent) solution in DCM (0.5 vol.) was added slowly to the reaction mixture, while maintaining the temperature at −15(±)5° C., and the obtained mixture was stirred for 1 hour at this temperature. Reaction progress was monitored by HPLC. Once the reaction was completed, the temperature was raised to 5(±)5° C. and aqueous saturated sodium bicarbonate solution (10 vol.) was added slowly. The obtained mixture was filtered through Celite bed and the Celite bed was washed with DCM (5 vol.). The organic layer was separated and the aqueous layer was extracted with DCM (5 vol.). The combined organic layers were washed with sodium chloride solution (5 vol.), and concentrated at 45(±)5° C. under atmospheric pressure. Methanol (2 vol.) was added to the residue and thereafter was distilled off under vacuum at 45(±5°) C.

Preparation of Compound 122 (FIG. 2; Acetyl Deprotection):

The product of previous step, containing Compound 121, was cooled to 10(±)5° C. and methanolic ammonia (25 v/w) was added. The reaction mixture was stirred at 30(±)5° C. for 24 hours, and reaction progress was monitored by HPLC. Once the reaction was completed, the reaction mixture was concentrated under vacuum at 40(±5°) C. Ethyl acetate (2 vol.) was added to residue and the solvents were co-distilled under vacuum at 40(±5°) C. The obtained mixture was cooled to 30(±)5° C., ethyl acetate (10 vol.) was added and the mixture stirred for 30-40 minutes, filtered, washed with water (2×10 vol.) and brine solution (10 vol.), dried over anhydrous sodium sulfate and concentrated under reduced pressure. The obtained residue was co-distilled with MTBE (2 v/w) at 40(±)5° C. and the mixture was cooled to 30(±5°) C. MTBE (20 v/w) was added and the mixture was stirred for 2 hours at 30(±5°) C. The product was filtered and washed with MTBE (2 vol.), yielding Compound 122 (85% yield; 98.2% purity as determined by HPLC).

Preparation of Compound 123 (ELX-02 Free Base; FIG. 2; CBz-Deprotection):

Compound 122 (1 mol equivalent) and MeOH (10 vol.) were mixed at 25±5° C., water (1 vol.) was added, and the obtained mixture was and stirred for 10-15 minutes. 10% Pd/C (0.25% w/w) was added and the obtained mixture was stirred for 24-36 hours at 25(±5) ° C. under hydrogen pressure. Reaction progress was monitored by TLC. Once the reaction was completed, the reaction mixture was filtered through Celite bed and the Celite bed was washed with MeOH. The filtrates were concentrated under vacuum at 45±5° C. The crude product (purity 95.8%) was purified by column chromatography.

Preparation of ELX-02 (FIG. 2, Salt Formation):

A mixture of ELX-02 free base (Compound 123, 1 mol equivalent) in MeOH (10 vol.) was stirred for 10-15 minutes and then cooled to 0-10° C. Pre-cooled methanolic H$_2$SO$_4$ (2.0 mol equivalents) solution was slowly added to the mixture at 0±5 OC, and the reaction mixture was stirred at 0-10° C. for 20-30 minutes, then at 30±5° C. for 1-2 hours, and was thereafter concentrated under vacuum at 45±5° C. Acetone (15 vol.) was added and the obtained mixture was stirred for 30 minutes at 25±5° C., filtered and the cake was washed with acetone (5 vol.), and dried under vacuum at 40±5° C. for 6 hours, yielding ELX-02 as a sulphate salt, featuring purity of 95.78% (Product: 76.36% and Sulfate peak: 19.42%), as determined by HPLC.

The structure of the obtained product was confirmed by H-NMR and Mass Spectra, presented in FIGS. 4 and 5, respectively.

Example 4

Read-Through Activity in Cell-Free Assay

Experimental Method:

The plasmids were transcribed in vitro and translated using rabbit reticulocytes (TNT mix) and then tested for the expression levels of the firefly and renilla luciferases. WT plasmids expressed both firefly and renilla luciferases while mutant plasmids expressed only the renilla luciferase due to the stop codon found in the inserted sequence. The read-through assays were conducted for the tested compounds and the controls by adding the compounds to the in vitro transcription/translation reaction mixture. In case the compounds exerted suppression of the premature nonsense/stop codon mutation, the firefly luciferase was expressed and a fold-change in its expression was observed.

Results:

Read-through activity of Rett Syndrome mutation R270X was tested using ELX-02 that was manufactured in Example 1 and 2, and the mutation suppression was calculated based on firefly/renilla expression ratio values, and normalized with respect to the expression level of the WT and the control sample (no tested compound).

FIGS. 6A-B present the results of Rett Syndrome mutation R270X nonsense mutation suppression dose-response cell-free assays conducted for ELX-02 according to embodiments of the present invention, at a concentration rage of 0-12 µM.

FIG. 6A presents stop-codon mutation read-through plot, showing percent read-through as a function of concentration of WT with ELX-02 (read-through to 50% renilla), comparing the read-through of the mutation, R270X, and FIG. 6B presents stop-codon mutation read-through plot, showing fold increase of read-through after exposure to ELX-02 from non-treated control as a function of ELX-02 concentration, comparing the read-through of the mutation R270X. ELX-02 showed dose-dependent increase in the read-through of the Rett Syndrome mutation, R270X.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A process of preparing a compound represented by Formula III:

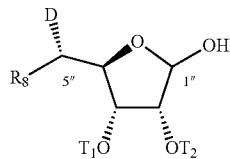

Formula III wherein: $OT_1$ and $OT_2$ are each independently a protected hydroxyl group;

$R_8$ is alkyl; and

D is a protected amino group, the process comprising:

reacting a compound represented by Formula IIIa:

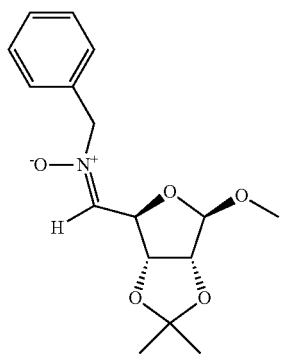

Formula IIIa with a Grignard reagent represented by a Formula $R_8MgX$, wherein X is halide, to thereby obtain stereoselectively a compound represented by Formula IIIb:

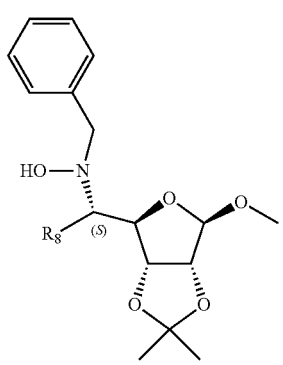

Formula IIIb converting said compound represented by Formula IIIb to a compound represented by Formula IIIc:

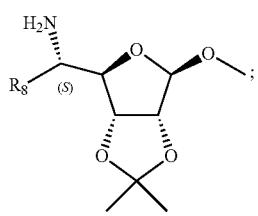

Formula IIIc reacting said compound represented by Formula IIIc with an amino-protecting group to thereby form said D; and reacting said compound represented by Formula IIIc with hydroxy protecting groups to thereby form said $OT_1$ and $OT_2$, thereby preparing the compound represented by Formula III.

2. The process of claim 1, wherein said amino-protecting group is N-benzyloxycarbonyl and/or each of said hydroxy-protecting groups is benzoyl.

3. The process of claim 1, wherein said compound represented by Formula IIIa is prepared by:

converting D-ribose to a dioxolane-protected D-ribose;

oxidizing a hydroxy group at position 5" to a respective aldehyde; and reacting said aldehyde with N-Benzyl hydroxyl amine hydrochloride.

4. The process of claim 1, wherein D is an N-benzyloxycarbonyl (CBz)-protected amino group, $R_8$ is methyl, and each of $T_1$ and $T_2$ is benzoyl.

5. The process of claim 3, wherein preparing said compound represented by Formula IIIa from D-ribose, reacting said compound represented by Formula IIIa with said Grignard reagent, converting said compound represented by Formula IIIb to said compound represented by Formula IIIc and reacting said compound represented by Formula IIIc with an amino-protecting group to thereby form said D, are performed in one reactor.

6. A process of preparing a pseudo-trisaccharide aminoglycoside compound represented by Formula Ia:

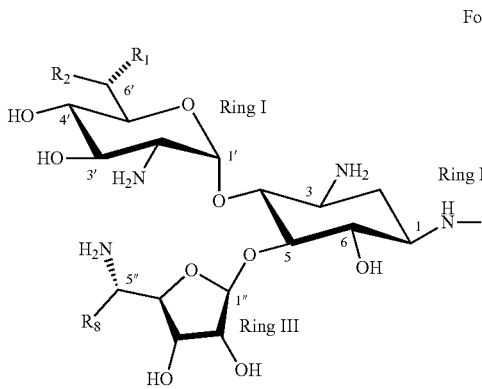

Formula Ia or a pharmaceutically acceptable salt thereof, wherein:

the dashed line represents an optional S-configuration or an R-configuration at position 6';

$R_1$ is selected from hydrogen, alkyl, cycloalkyl or aryl;

$R_2$ is selected from a substituted or unsubstituted alkyl, OR' and NR'R", wherein each of R' and R" is independently selected from hydrogen, a substituted or unsubstituted alkyl, a substituted or unsubstituted cycloalkyl, a substituted or unsubstituted aryl, a substituted or unsubstituted heteroaryl, a substituted or unsubstituted alkaryl, and an acyl;

$R_4$ is selected from hydrogen, acyl, an amino-substituted alpha-hydroxy acyl, a substituted or unsubstituted alkyl, a substituted or unsubstituted cycloalkyl, a substituted or unsubstituted aryl, a substituted or unsubstituted alkaryl, and a cell-permealizable group; and $R_8$ is alkyl, the process comprising:

preparing a compound represented by Formula III, according to claim 1;

converting said compound of Formula III to an activated form; and coupling said activated form of the compound represented by Formula III with a compound represented by Formula IIb:

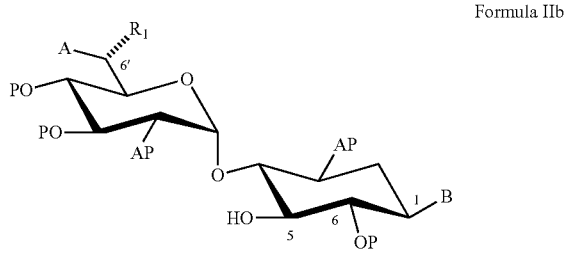

Formula IIb wherein:

the dashed line represents an optional S-configuration or an R-configuration at position 6';

OP is a protected hydroxyl group;

AP is a protected amino group;

A is a protected hydroxyl group, when $R_2$ in Formula Ia is OR' and R' is hydrogen; a protected amino group, when $R_2$ is Formula Ia is NR'R" and at least one of R' and R" is hydrogen; or is a protected or unprotected form of a group defining $R_2$ when $R_2$ is other than OH, $NH_2$, NHR' or NHR";

B is a protected amine group, when $R_4$ is Formula Ia is hydrogen, or a protected or unprotected form of a group defining $R_4$ when $R_4$ is other than hydrogen;

de-protecting said protected hydroxyl groups;

de-protecting said protected amino groups; and de-protecting said protected form of a group defining $R_2$ and/or said protected form of a group defining $R_4$, if present, thereby preparing a compound represented by Formula Ia.

7. The process of claim 6, wherein said converting said compound of Formula III to said activated form is performed in situ, without isolating said activated form.

8. The process of claim 6, wherein each OP is O-acetyl.

9. The process of claim 6, wherein each AP is an N-benzyloxycarbonyl (CBz)-protected amino group.

10. The process of claim 6, wherein the compound of Formula Ia is a sulfate salt, the process further comprising converting a compound represented by Formula Ia in a form of a free base thereof to said sulfate salt.

11. The process of claim 8, wherein when A is a protected hydroxyl group, A is O-acetyl.

12. The process of claim 9, wherein when A is a protected amino group, A is CBz-protected amino group.

13. The process of claim 8, wherein de-protecting OP is effected in a methanolic ammonia solution.

14. The process of claim 10, wherein said converting is performed by contacting a compound represented by Formula Ia in a form of a free base thereof with a methanolic solution of sulfuric acid ($H_2SO_4$).

* * * * *